(12) United States Patent
Plöchinger

(10) Patent No.: US 9,606,074 B2
(45) Date of Patent: Mar. 28, 2017

(54) FLUID PROPERTY SENSOR WITH HEAT LOSS COMPENSATION AND OPERATING METHOD THEREOF

(71) Applicant: Heinz Plöchinger, Freinberg (AT)

(72) Inventor: Heinz Plöchinger, Freinberg (AT)

( * ) Notice: Subject to any disclaimer, the term of this patent is extended or adjusted under 35 U.S.C. 154(b) by 749 days.

(21) Appl. No.: 13/953,708

(22) Filed: Jul. 29, 2013

(65) Prior Publication Data

US 2014/0026640 A1    Jan. 30, 2014

Related U.S. Application Data

(60) Provisional application No. 61/677,398, filed on Jul. 30, 2012.

(51) Int. Cl.
*G01N 25/18* (2006.01)
*G01L 21/12* (2006.01)

(52) U.S. Cl.
CPC ............. *G01N 25/18* (2013.01); *G01L 21/12* (2013.01)

(58) Field of Classification Search
CPC .............................. G01L 21/12; G01N 25/18
See application file for complete search history.

(56) References Cited

U.S. PATENT DOCUMENTS

| | | | |
|---|---|---|---|
| 1,993,063 A * | 3/1935 | Klopsteg | G01L 21/10 136/223 |
| 5,597,957 A | 1/1997 | Schieferdecker et al. | |
| 6,023,979 A * | 2/2000 | Bills | G01L 21/12 73/753 |
| 7,360,415 B2 | 4/2008 | Nakano et al. | |
| 7,497,118 B2 | 3/2009 | Ploechinger | |
| 7,642,923 B2 | 1/2010 | Ploechinger | |
| 8,047,711 B2 | 11/2011 | Ploechinger | |
| 8,449,177 B2 | 5/2013 | Kvisteroy et al. | |

FOREIGN PATENT DOCUMENTS

| | | |
|---|---|---|
| DE | 19903010 | 8/2000 |
| EP | 0660096 | 6/1995 |
| EP | 1409963 | 4/2004 |
| JP | 402082145 A * | 3/1990 |

OTHER PUBLICATIONS

Heinz Plöchinger, 2002, "Fortschritt in der Vakuum-Messtechnik", Vakuum in Forschung und Praxis, vol. 14, No. 5, pp. 281-283.
W. Jitschin & S. Ludwig, 2004, "Dynamical behaviour of the Piranisensor", Vacuum, vol. 75, pp. 169-176.

* cited by examiner

*Primary Examiner* — Laura Martin
*Assistant Examiner* — Alex Devito
(74) *Attorney, Agent, or Firm* — Smartpat PLC

(57) ABSTRACT

An improved Pirani sensor uses a measuring element disposed within a fluid between a base plate and a cover. The measuring element is held by suspension members that are connected to the base plate. A heating element is thermally conductively connected to the suspension members. Using the sensor the characteristic of the fluid is determined by evaluating the heat transfer from the thermal element through the fluid into the cover when heating power is applied to measuring element. Parasitic conductive heat loss from the measuring element into the suspension members is compensated by applying power to the heating element.

18 Claims, 24 Drawing Sheets

PRIOR ART

PRIOR ART

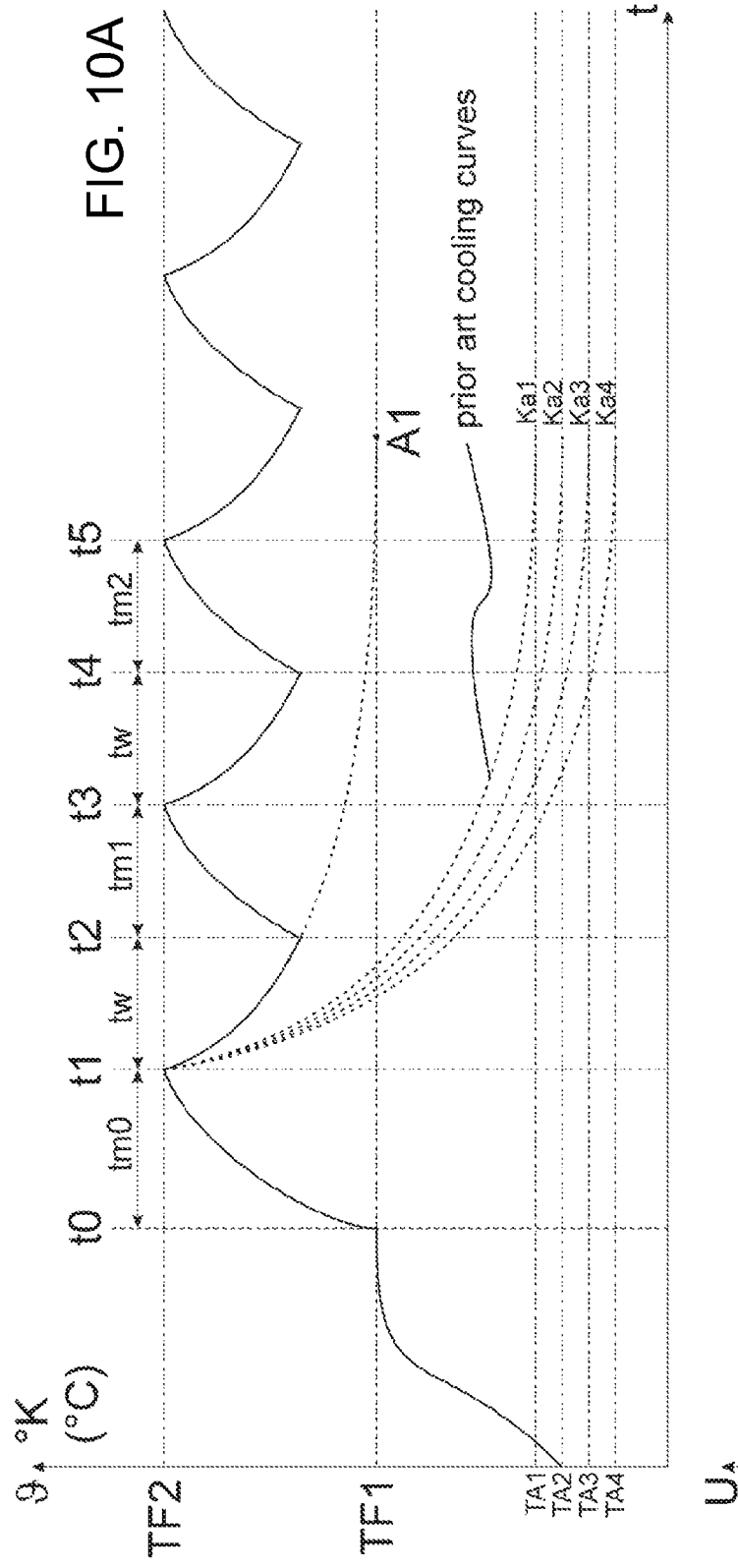

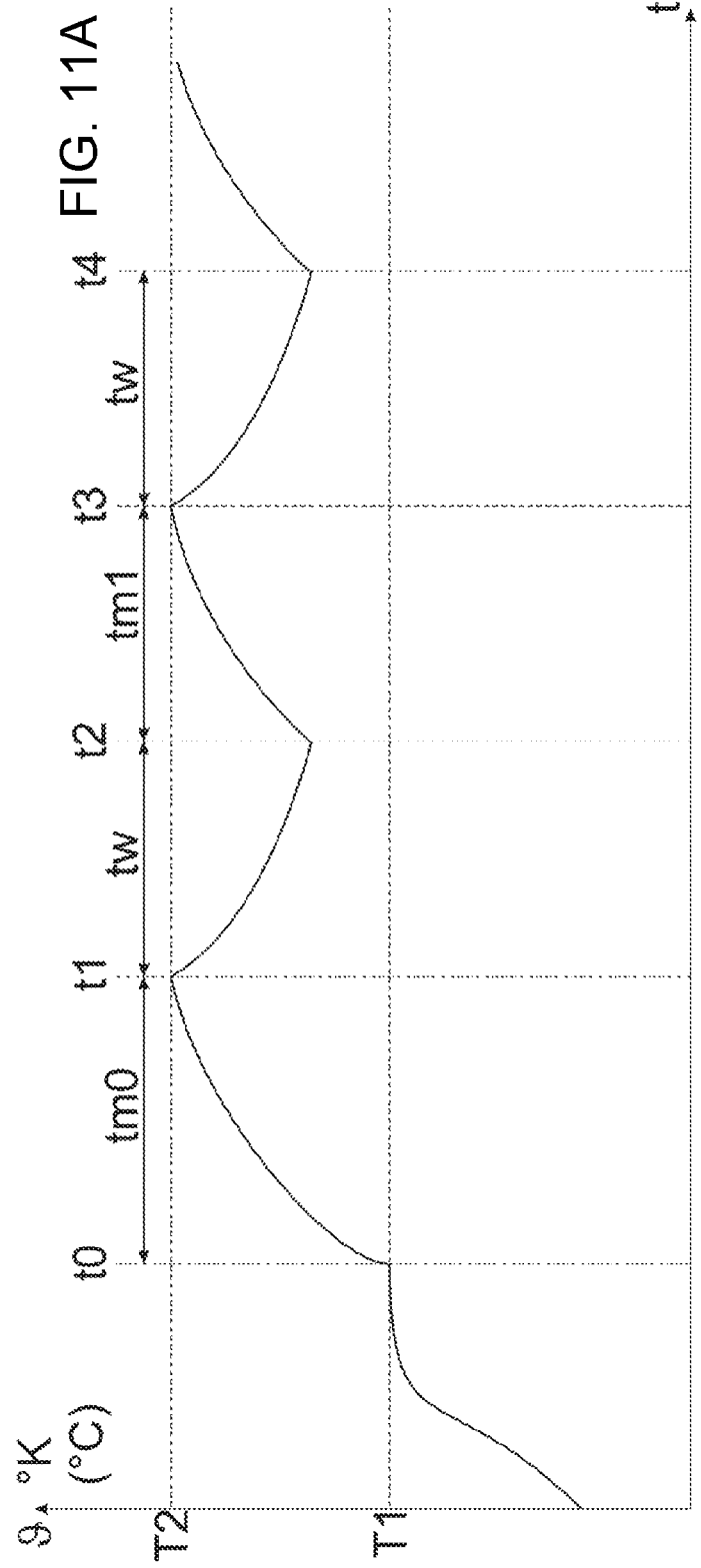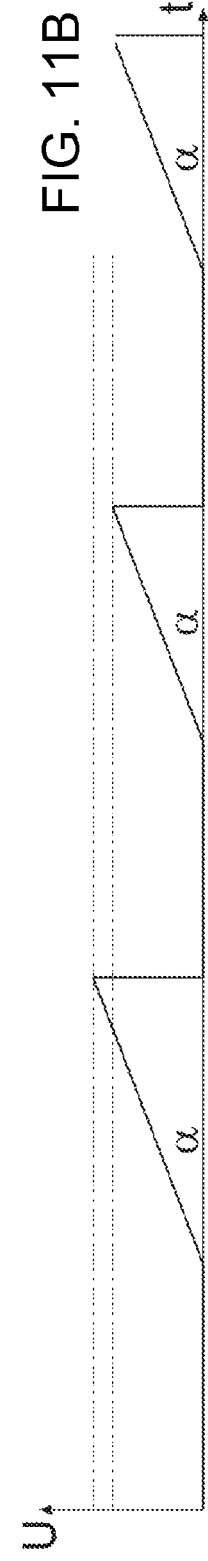

US 9,606,074 B2

FLUID PROPERTY SENSOR WITH HEAT LOSS COMPENSATION AND OPERATING METHOD THEREOF

TECHNICAL FIELD

The present disclosure generally relates to thermal sensors for measuring fluid characteristics which change with thermal conductivity and heat capacity of a fluid, and more particularly, to Pirani sensors for measuring gas pressure.

BACKGROUND

A Pirani sensor consists of a measuring element suspended in a tube which is connected to the system whose vacuum is to be measured. The measuring element is typically a heated metal wire (also called a filament). A filament suspended in a gas will lose heat to the gas as its molecules collide with the wire and remove heat. If the gas pressure is reduced the number of molecules present will fall proportionately and the wire will lose low heat more slowly. Measuring the heat loss is an indirect indication of pressure. The filament is connected to an electrical circuit from which, after calibration, a pressure reading may be taken.

Exemplary Pirani sensors are disclosed in German patent no. DE19903010 and in European patents No. EP0660096 and EP1409963. Further exemplary sensors and their operating modes are disclosed in U.S. Pat. Nos. 7,360,415; 7,497,118; 7,642,923 and 8,047,711 which are hereby incorporated herein by reference in their entireties.

While the heat loss from the filament into the gas is an indicator of the gas pressure, conventional Pirani sensors also experience conductive heat loss from the filament into the filament's suspension and radiation heat losses from the filament. During operation the conductive heat loss into the suspension ($P_{suspension}$) and radiation heat loss ($P_{radiation}$) add up to a base power $P_{zero}$ which is required to maintain the operating condition of the sensor. This base power may also be referred to as "zero pressure" $p_0$, indicating the pressure that would lead to the same heat loss into the gas as the parasitic effects of conductive and radiation heat loss in a complete vacuum.

The base power $P_{zero}$ of a Pirani sensor depends on the sensor's geometry, material properties, and environmental conditions in which the sensor operates, especially the ambient temperature. The material properties that affect base power include the emission coefficient of the measuring element (filament) surface and reflection properties of the surface into which power is transferred by radiation. While the influence of the geometry, for example the thickness of the heat dissipating suspension pins, and the influence of the material properties may be assumed to be design related constants, the influence of the ambient temperature is variable.

The greater the amount of parasitic heat losses and therefore the base power $P_{zero}$, the more difficult the detection of small changes in the thermal conductivity, heat capacity, pressure or flow of the measured fluid becomes.

Goal in the design of such sensors is therefore a minimization of base power $P_{zero}$. For reasons of mechanical stability, however, there is a tight limit to reducing the dimensions of the measuring element's suspensions. The suspension must be capable of carrying the measuring element, which may be a (metal) wire, measuring filaments, or a membrane that carries measuring elements.

Conventional approaches have attempted to compensate for changing ambient influences, such as ambient temperature, by additional measuring resistors in the electrical evaluation circuit to which the sensor is connected. Those approaches are, however, limited. Since the ambient influence on a Pirani sensor depends not only on the temperature but also on the pressure of the measured fluid, compensation by a temperature sensor is, strictly speaking, valid only for a single operating point.

SUMMARY

The present disclosure provides an improved thermal conductivity sensor for measuring a characteristic of a fluid which substantially reduces the parasitic heat loss through the measuring element's suspension and radiation heat losses from the measuring element. The reduced heat losses result in a reduced base power $P_{zero}$ and zero pressure $p_0$. The reduced base power $P_{zero}$ improves the signal to noise ratio of the sensor, and correspondingly the sensor's accuracy. The improved sensor also reduces or eliminates surface contamination of the measuring element, or reduces its effect on the measurement.

The improved sensor uses a measuring element disposed within a fluid adjacent to a heat sink. The measuring element may for example be a metal wire, a filament, or a flat meander-shaped metal foil. The measuring element is held by suspension members. The suspension members may be connected to a base plate. The suspension members may for example be electrically conductive suspension pins or be a silicon structure in case of a micro-Pirani sensor chip. A suspension heating element is thermally conductively connected to the suspension members. The suspension heating element may be a heating resistor. Alternatively, two suspension heating elements may be used, one each thermally conductively attached to two suspension members.

The thermal conductivity sensor may be used to determine the flow rate of a fluid across the sensor, or to identify a fluid based on its thermal conductivity. An important application of the sensor is its use as a Pirani sensor to measure gas pressure in a vacuum. When used as a Pirani sensor, pressure of the gas around the sensor is determined by evaluating the heat transfer from the thermal element through the gas into the adjacent heat sink when heating power is applied to measuring element. While measuring the heat transfer through the gas, a Pirani sensor traditionally experiences parasitic conductive heat loss from the measuring element into the suspension members. In the here presented sensor this parasitic heat loss is compensated by applying compensation power to the suspension heating element. The compensation power is preferably chosen such, that the suspension members are heated to approximately the same temperature as the measuring element. The compensation power may partially reduce or completely eliminate parasitic suspension heat loss. The compensation power may e.g. reduce the parasitic suspension heat loss by more than 90%.

In another application the characteristic of the liquid or gaseous fluid that is to be measured may be the fluid's flow rate. While the concept presented in this paper is primarily based on use of a heating element that is thermally conductively connected to the suspension members, temperature control of the suspension members may also be based on use of a cooling element, for example a Peltier element. This may be useful in special applications such as measuring flow in cold fluids.

The heat sink is positioned near the measuring element and serves as a heat exchange surface to enable conductive heat flow through the fluid that is to be measured. The heat sink may simultaneously serve as a cover of the sensor and protect the measuring element from damage and contamination. To control the temperature of the heat sink it may be thermally conductively connected to a heat sink heating element.

The sensor is controlled by a control processor, which is operatively connected to the measuring element and to the suspension heating element. The control processor is configured to determine the temperature of the measuring element. The control processor may also be configured to determine the temperature of the heating element. Various operating methods exist. In a preferred method the control processor applies power to the heating element to maintain a substantially constant temperature $T_1$. The control processor further applies pulsed power to the measuring element until the measuring element reaches a predetermined temperature $T_2$.

The sensor may be calibrated by exposing it to an ultra-high vacuum, ideally at or below its lower sensing range. During calibration power to the suspension heating element is adjusted, until the voltage across a bridge circuit into which the measuring element is connected reaches a lower threshold. Calibration of suspension heating may be based on adjusting a variable resistance which is operatively connected to a suspension heating control element. Alternatively, calibration may be based on storing a value in non-volatile memory, which is used by the control processor to control the suspension heating element.

The measuring element may be connected to an electronic circuit which comprises an upper threshold comparator operatively connected to the control processor for detecting an upper temperature threshold of the measuring element. The control processor applies, through a variable voltage generator, power to the measuring element until a signal from the upper threshold comparator is received. The control processor then turns off or substantially reduces the output of the variable voltage generator for a predetermined time $t_w$ after the signal from the upper threshold comparator is received Instead of letting the measuring element cool down for a predetermined time $t_w$, cooling of the measuring element may be based on letting it cool to a predetermined intermediate temperature. This is accomplished by the addition of an intermediate threshold comparator operatively connected to the control processor for detecting an intermediate temperature threshold of the measuring element. In this case the control processor applies, through a variable voltage generator, power to the measuring element until a signal from the upper threshold comparator is received, and turns off or substantially reduces the output of the variable voltage generator until a signal from the intermediate threshold comparator is received A beneficial operation of the sensor is achieved when $T_1$ is about 60° C.-120° C. and $T_2$ is about 80° C.-140° C. $T_2$ should be selected to be about 20° C. higher than $T_1$, beneficially between 10° C. and 40° C. higher than $T_1$.

A method for measuring a characteristic of a fluid comprises disposing a measuring element within a fluid, the measuring element being held by suspension members. Measuring power is applied to the measuring element, either constantly or in pulses. If pulses are used to power the measuring element those may be of constant voltage or current, or following a characteristic curve, e.g. a voltage or currant ramp with a known ramp angle α. In pulse operation measuring power is applied until the measuring element reaches an upper temperature of $T_2$.

Compensation power is applied to one or more suspension heating elements which are thermally conductively connected to the suspension members. The compensation power is selected to compensate, at least partially, parasitic conductive heat loss from the measuring element into the suspension members.

The heat transfer from the thermal element through the fluid to the cover by measuring the power applied to the measuring element is evaluated, and a characteristic of the fluid is derived. Evaluation of the heat transfer from the thermal element into the fluid is achieved by measuring a time $t_x$ required to heat the measuring element from a first temperature $T_1$ to a second temperature $T_2$. Subsequently a characteristic of the fluid is derived by calculating a measure from the time $t_x$.

In pulsed operation, following the heating of the measuring element to temperature $T_2$ power is removed, allowing the measuring element to cool down. Following the application of measuring power a predetermined wait period $t_w$ may be applied until a subsequent application of measuring power, and the frequency $1/(t_x+t_w)$ may be used to derive the desired characteristic of the fluid. Other mathematical calculations based on $t_x$ and $t_w$ may also be used.

The following detailed description is merely exemplary in nature and is not intended to limit the invention or the application and uses thereof. Furthermore, there is no intention to be bound by any theory presented in the preceding background or the following detailed description.

BRIEF DESCRIPTION OF THE DRAWINGS

FIG. 10A is a diagram to illustrate temperature and voltage of a Pirani sensor over time when used in an electronic circuit as in FIG. 10D.

FIG. 10B is a diagram to illustrate heating pulses applied to the Pirani sensor as in FIG. 10A.

FIG. 10C is a diagram to illustrate alternatively shaped heating pulses applied to the Pirani sensor as in FIG. 10A.

FIG. 11A shows the diagram of FIG. 10A using an alternative control.

FIG. 11B shows the diagram of FIG. 10B using an alternative control.

FIG. 11C shows the diagram of FIG. 10C using an alternative control.

DETAILED DESCRIPTION

Figure 1A:
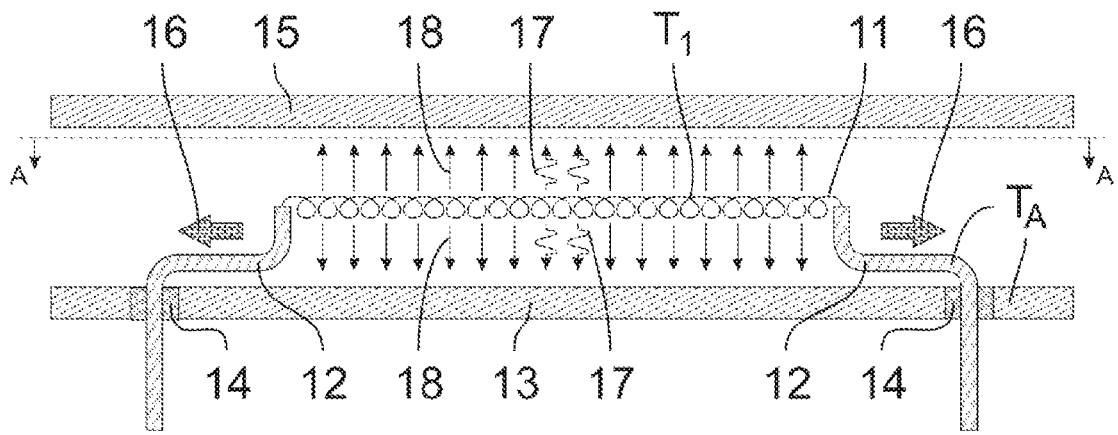
FIG. 1A is a side sectional view of a prior art Pirani sensor.
Figure 1B:
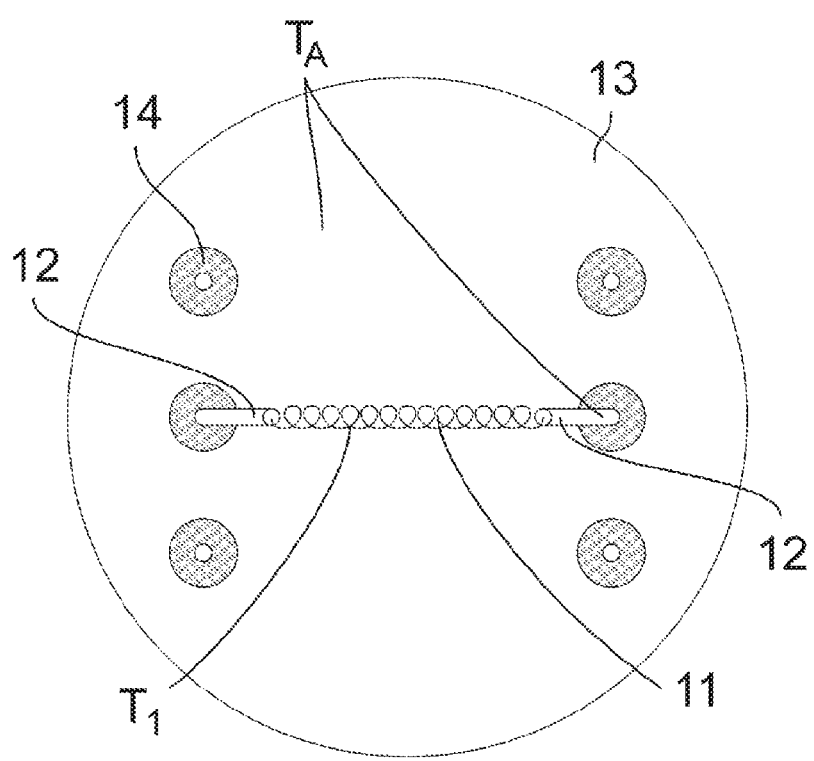
FIG. 1B is a top sectional view A-A of the sensor as in FIG. 1A.

Referring to FIG. 1A and FIG. 1B, a sectional side and top view of a conventional Pirani vacuum sensor are shown. A measuring element 11 is suspended within a fluid. The measuring element 11 is a filament made of coiled metal wire. The measuring element 11 is held on both ends by suspension pins 12, which are electrically conductive. The suspension pins 12 reach through insulated bushings 14 in a base plate 13. The lower ends of the suspensions pins 12 reach outside the sensor and are used to electrically connect the measuring element 11 to an electric circuit. A heat sink 15 is positioned adjacent to the measuring element 11. The heat sink 15 may serve as a sensor cover.

During operation the base plate 13 and the suspension pins 12 assume ambient temperature $T_A$. Through externally provided power the measuring element 11 is heated to a controlled temperature $T_1$. The measuring element 11 transfers heat into the surrounding fluid by thermal conduction. Fluid heat transfer 18 from the measuring element 11 to the heat sink 15 and the base plate 13 is illustrated by thin straight arrows. Heat transfer into the fluid is a signal, which can be used to determine characteristics of the fluid, e.g. the fluid's pressure, flow rate or composition. The measuring element 11 also conductively transfers heat into suspension pins 12. The suspension heat loss 16 is illustrated by bold arrows. The measuring element 11 further transfers heat into the cover 15 and the base plate 13 by radiation. This radiation heat loss 17 is indicated by wavy arrows.

Figure 2A:
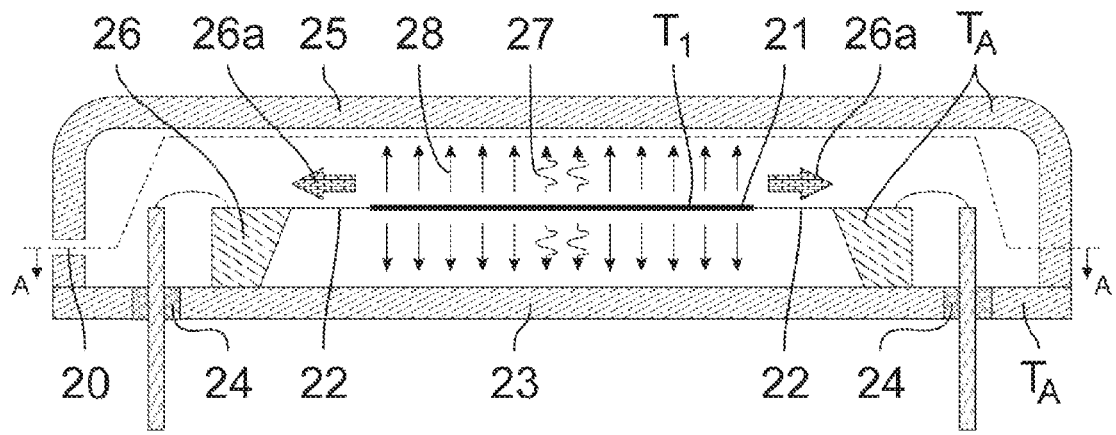
FIG. 2A is a side sectional view of a prior art micro-Pirani sensor.
Figure 2B:
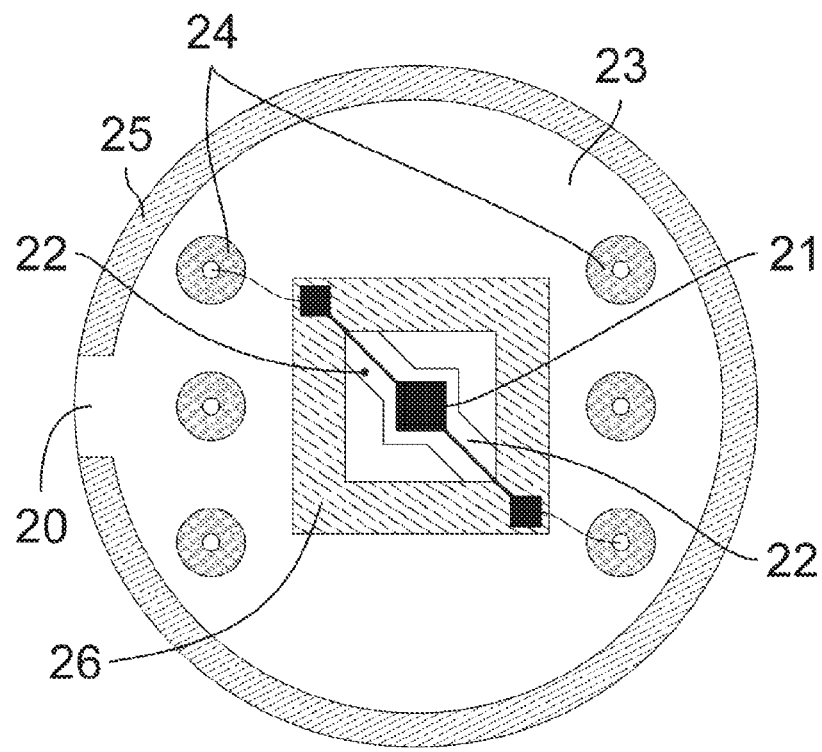
FIG. 2B is a top sectional view A-A of the sensor of as in FIG. 2A.

Referring now to FIG. 2A and FIG. 2B a sectional side and top view of a conventional micro-Pirani vacuum sensor are shown. A thin micromachined membrane measuring element 21 is suspended in a fluid. The membrane measuring element 21 is connected by electrically and thermally conductive suspension leads 22 to a micro-Pirani chip 26. The micro-Pirani chip 26 is disposed on base plate 23. The membrane measuring element 21 is electrically connected to leads which lead through bushings 24 in the base plate 23. The micro-Pirani sensor is enclosed by a cover 25. The cover 25 has an opening 20 allowing fluid to enter and exit the sensor.

During operation the base plate 23 and the cover 25 assume ambient temperature $T_A$. Through externally provided power the membrane measuring element 21 is heated to a controlled temperature $T_1$. The membrane measuring element 21 transfers heat into the surrounding fluid by thermal conduction. Fluid heat transfer 28 is illustrated by thin straight arrows. Heat transfer into the fluid is a signal, which can be used to determine characteristics of the fluid, e.g. the fluid's pressure, flow rate or composition. The membrane measuring element 21 also conductively transfers heat into suspension leads 22. Suspension heat loss 26a is illustrated by bold arrows. The membrane measuring element 21 further radiates heat into the cover 25 and the base plate 23. Radiation heat loss 27 is indicated by wavy arrows.

The prior art sensors of FIGS. 1 and 2, when used as a Pirani vacuum sensors, have a zero pressure corresponding to the sum of the suspension heat losses 16, 26a and the radiation heat losses 17, 27. Typically, the conductive heat loss 26a of a micro-Pirani sensor is lower than the conductive heat loss 16 of a larger Pirani sensor, and correspondingly the zero pressure of a micro-Pirani sensor as shown in FIG. 2 is lower than that of a larger Pirani sensor as shown in FIG. 1. The same applies to the base power when the sensors are used as fluid flow sensors.

Figure 3A:
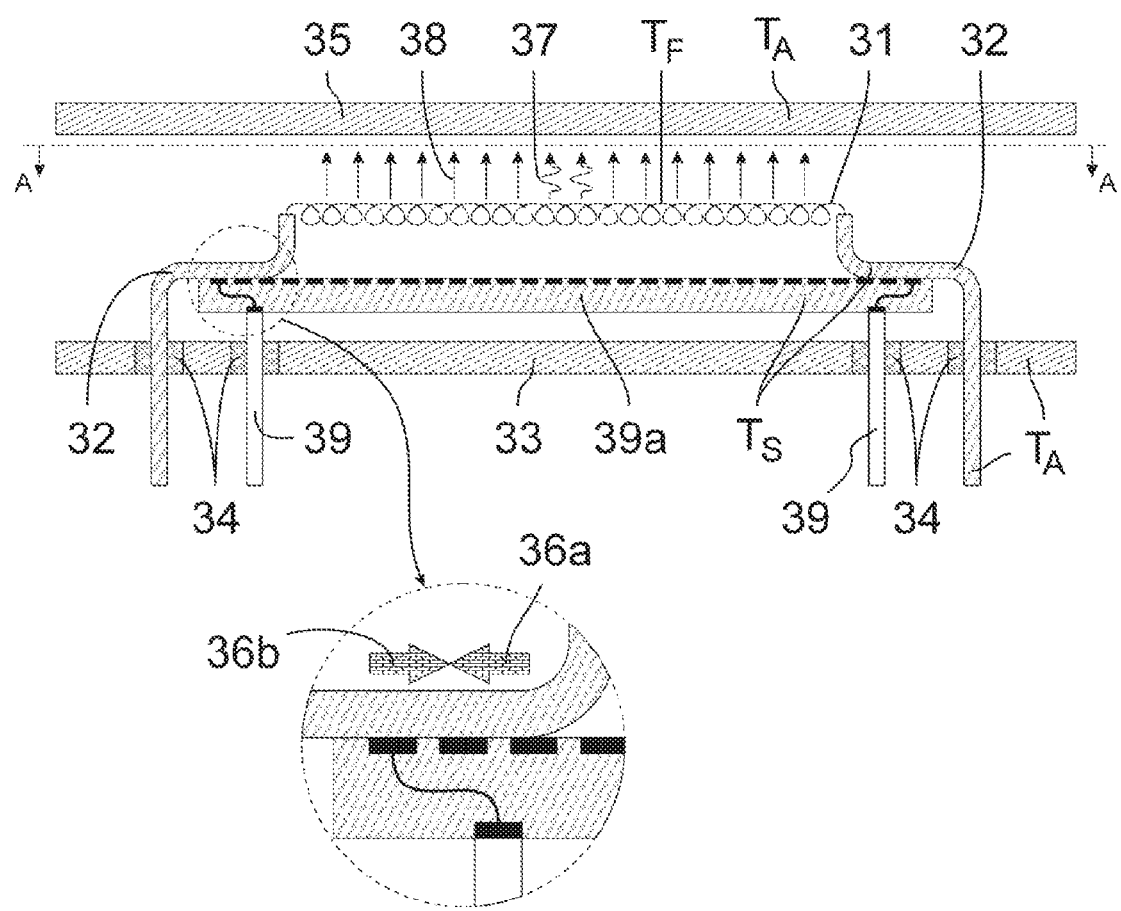
FIG. 3A is a side sectional view of a Pirani sensor with a suspension heating element for loss compensation.
Figure 3B:
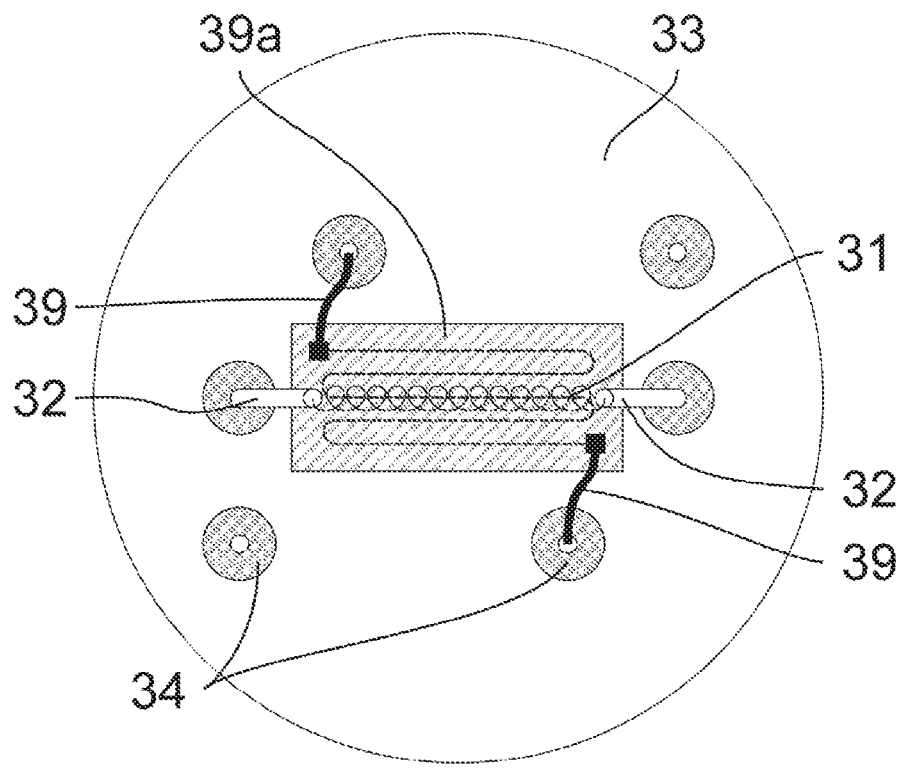
FIG. 3B is a top sectional view A-A of the sensor as in FIG. 3A.
Figure 3C:
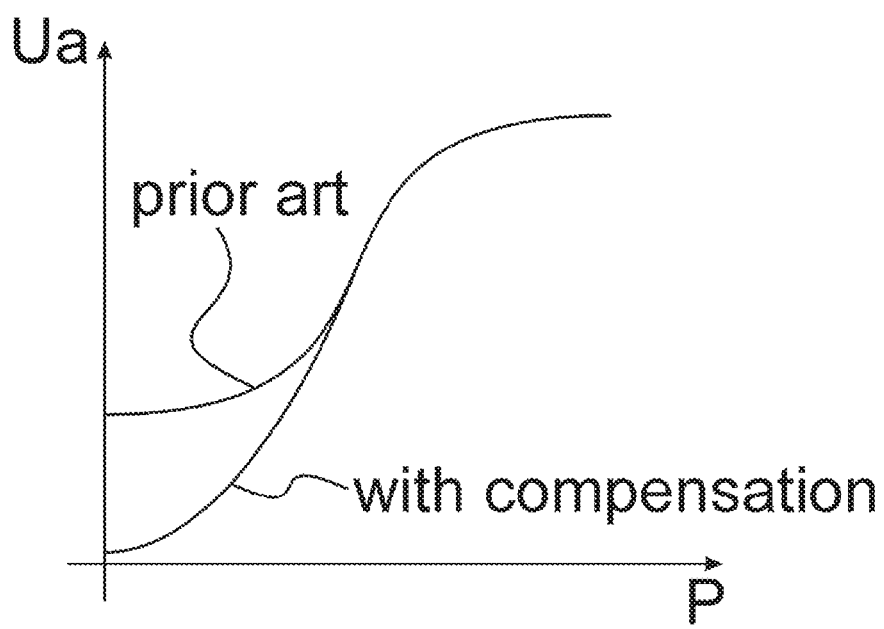
FIG. 3C is a schematic diagram comparing the operating characteristics of sensor with and without heat loss compensation.

FIG. 3A and FIG. 3B show an improved version of the Pirani sensor as in FIG. 1A and FIG. 1B. A measuring element 31 is suspended within a fluid. The measuring element 31 is a filament made of coiled metal wire. The measuring element 31 is held on both ends by suspension pins 32, which are electrically conductive. The suspension pins 32 reach through insulated bushings 34 in a base plate 33. The lower ends of the suspensions pins 32 reach outside the sensor and are used to electrically connect the measuring element 31 to an electronic circuit. Positioned adjacent to the measuring element 31 is a heat sink 35. The heat sink 35 may be a cover which encloses the sensor and also acts as a heat exchange surface.

A heating element 39a is disposed underneath the measuring element 31 and thermally conductively connected to the suspension pins 32. The heating element 39a is electrically connected to electrical terminals 39 which reach through bushings 34 in the base plate 33. The heating element 39a may dual-function as a temperature sensor to measure the temperature of the suspension pins 32 and, for example, be a resistance thermometer (Pt100, Pt1000, Ni100, Ni1000).

During operation the base plate 33 and the lower ends of the suspension pins 32 assume ambient temperature $T_A$. Through externally provided power the measuring element 31 is heated to a controlled temperature $T_F$. The measuring element 31 transfers heat into the surrounding fluid by thermal conduction. Fluid heat transfer 38 is illustrated by thin straight arrows. Heat transfer through the fluid occurs primarily between the measuring element 31 and the heat sink 35, which acts as a heat exchange surface. Heat transfer through the fluid is a signal, which can be used to determine characteristics of the fluid, e.g. the fluid's pressure, flow rate or composition. The measuring element 31 also conductively transfers heat into the suspension pins 32. Suspension heat loss 36a is illustrated by bold arrows. The measuring element 31 further transfers heat into the heat sink 35 and the base plate 33 by radiation. Radiation heat loss 37 is indicated by wavy arrows.

Externally provided power to the heating element 39a through the electrical terminals 39 provides conductive heat loss compensation 36b which counteracts the conductive heat loss 36a into the suspension pins 32. The externally provided power to the heating element 39a will also be referred to as compensation power ($P_{comp}$). The compensation power is selected to at least partially replace the power otherwise discharged by thermal conduction of the suspension and thus minimize the effect of the base power on the actual measurement at the measuring element. The zero pressure of a Pirani measuring range can be significantly reduced, and the measuring range can be extended towards lower pressures.

A traditional Pirani sensor without heat loss compensation, when measuring a vacuum of $10^{-4}$ mbar, may operate with a measuring element voltage of about 300 mV and a measuring element current of about 2 mA. The measuring element hence experiences a total heat transfer of about 600 µW. Only 0.1% of this total heat transfer is typically caused by conductive heat transfer through the gas in the vacuum, and 99.9% of the heat is lost through the suspension and through radiation. The low signal portion of the total power which is measured limits the operating range of a traditional Pirani sensor. By applying compensation power to reduce suspension heat loss, the signal portion of the overall power applied to the measuring element can be significantly improved. This allows an extended measuring range of down to e.g. $10^{-6}$ mbar. Generally speaking, if the suspension is at the same temperature as the measuring element, no heat flows from the measuring element into the suspension. The suspension may for example be two suspension pins 32, a bracket, or part of a microchip. Ideally, heat losses at the measuring element 31 will occur only through the thermal conductivity of the surrounding fluid and through radiation losses, primarily in the direction of the heat sink 35.

Variation of a fluid's environmental conditions primarily influences heat flow through the suspension, and to a much lesser extent radiation losses. The ability to control and reduce suspension heat losses hence provides a significant improvement. However, when measuring very low pressures, variable radiation losses and deposits on the surface of a measuring element can still be disturbing. To minimize also the remaining environmental effect on the measurement noise, radiation losses can be reduced in three possible ways:
 1. The absolute temperature of the measuring element can be reduced, thus making it less prone to radiating heat.
 2. The temperature offset between the measuring element and the corresponding heat sink may be reduced.
 3. Highly reflective surfaces may be used.

In a simplified model the measuring element suspension pins 32 and the heating element 39 can be represented by a plate with temperature $T_S$ and an area A. The heat sink 35 can be represented as a coplanar plate at temperature $T_A$ and area A. Assuming $T_m$ is a mean temperature between $T_S$ and $T_A$ with $T_m=(T_S+T_A)/2$ then the total radiation loss $P_{rad}$ is $$P_{rad}=4AE\sigma T_m^3(T_S-T_A),$$

wherein E=radiation exchange factor and σ=Boltzmann constant.

The radiation exchange factor E is composed of the emission coefficient and the reflection coefficient of the radiating and absorbing elements in the arrangement. E depends on the materials used and their surface. Highly reflective surfaces reduce E and thereby the entire exchanged radiation power.

If the offset between $T_S$ and $T_A$ decreases, so does the radiation loss. A reduction of the mean temperature $T_m$ has a significant effect, since the radiation loss decreases with the cube of the absolute temperature $T_m$. The radiation loss portion of the total signal of a Pirani sensor operating at 400 K is about 3 times higher than if the measuring element is regulated at e.g. 350 K at the same ambient temperature of 20° C.

The disclosed arrangement allows an operation with the measuring element being heated to about 353.1K (80° C.). If the adjacent transfer surface (heat sink) is controlled to a temperature of 333.1K (60° C.), the difference $T_S-T_A=20K$, and thus considerably smaller than typical Pirani sensors according to the prior art. Temperature control of the heat sink will be described in more detail below. A difference of only about 20K between $T_S$ and $T_A$ reduces the desirable heat transfer through the fluid which is the signal to be measured. However, the associated radiation power loss decreases faster than the desired signal, leading to an improved signal to noise ratio. By lowering the operating temperature of the measuring element, and reducing the temperature offset between the measuring element and the surrounding heat exchange surface (heat sink) as described, the signal to noise ration can be improved by approximately a factor of 5.

Further improvements are possible by choosing a highly reflective surface for the measuring element 31, the suspension pins 32, and the heat sink 35. The reflective surfaces reduce radiation exchange factor E and correspondingly the radiation losses.

The shape of the heat sink 35 is influenced by its functions as a heat exchange surface and cover to protect the measuring element 31 from damage and contamination. Due to the need of fluid (gas or liquid) exchange, the heat sink 35 may only inadequately protect the measuring element 31 against contamination. Nevertheless occurring contamination of the measuring element surface, for example due to condensation, can be partially eliminated by short-term heating of the measuring element 31 to a higher target temperature.

Figure 4A:
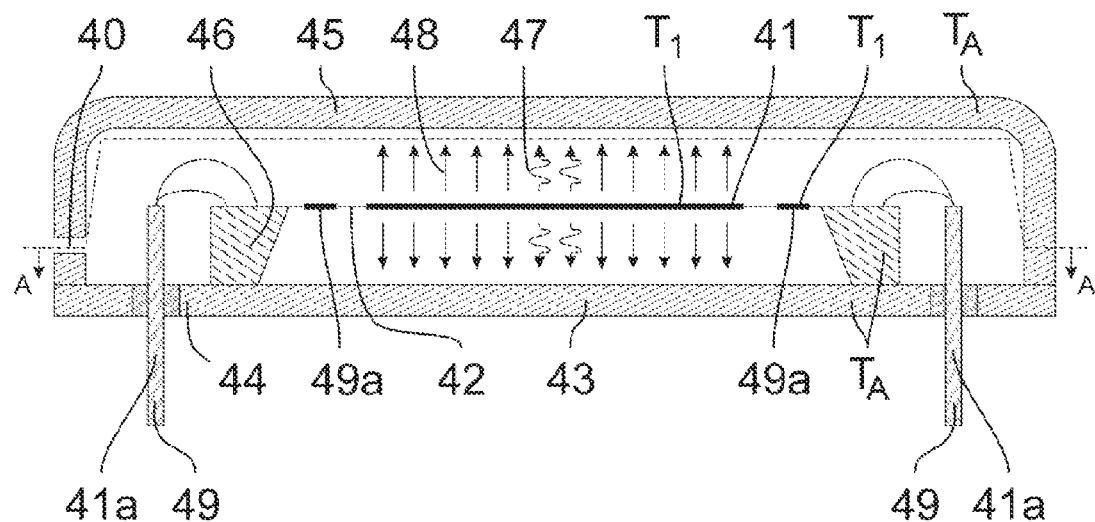
FIG. 4A is a side sectional view of a micro-Pirani sensor with suspension heating elements for loss compensation.
Figure 4B:
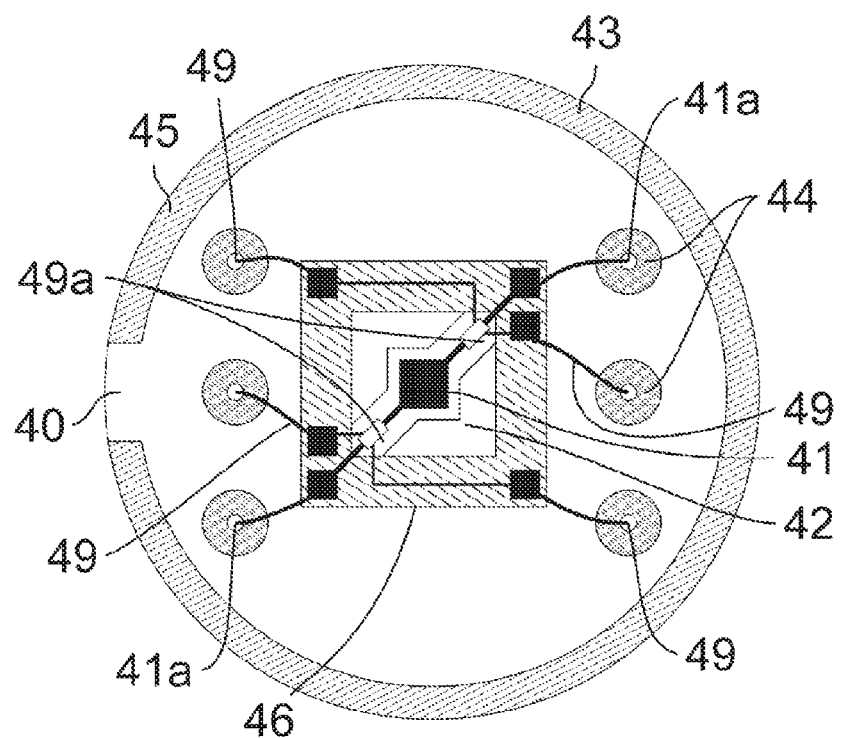
FIG. 4B is a top sectional view A-A of the sensor as in FIG. 4A.

FIG. 4A and FIG. 4B show an improved version of the Pirani sensor as in FIG. 2A and FIG. 2B. A thin micromachined membrane measuring element 41 is suspended in a fluid. The membrane measuring element 41 is connected by electrically and thermally conductive suspension leads 42 to a micro-Pirani chip 46. The micro-Pirani chip 46 is disposed on a base plate 43. The membrane measuring element 41 is electrically connected to leads 41a which lead through bushings 44 in the base plate 43. The micro-Pirani sensor is enclosed by a cover 45. The cover 45 has an opening 40 allowing fluid to enter and exit the sensor. The cover 45 also functions as a heat sink.

Heating elements 49a are disposed on the suspension leads 42 and electrically connected to terminals 49 which reach through bushings 44 in the base plate 43. As shown, one heating element 49a is placed on each of the two suspensions leads 42 that hold the membrane measuring element 41. Both heating elements 49a are internally wired in parallel to terminals 49. Alternatively, both heating elements could be wired in series.

During operation the base plate 43, the micro-Pirani chip 46 and the cover 45 assume ambient temperature $T_A$. Through externally provided power the membrane measuring element 41 is heated to a controlled temperature $T_1$. The membrane measuring element 41 transfers heat into the surrounding fluid by thermal conduction. Fluid heat transfer 48 is illustrated by thin straight arrows. Heat transfer into the fluid is a signal, which can be used to determine characteristics of the fluid, e.g. the fluid's pressure. The membrane measuring element 41 also conductively transfers heat into the suspension leads 42. Suspension heat loss 46a is illustrated by bold arrows. The membrane measuring element 41 further radiates heat into the cover 45 and the base plate 43. Radiation heat loss 47 is indicated by wavy arrows.

Externally provided power to the heating elements 49a through the electrical terminals 49 provides heat loss compensation 46b which counteracts the conductive heat loss 46a. In sum, no conductive heat is lost through suspension leads 42.

Figure 5A:
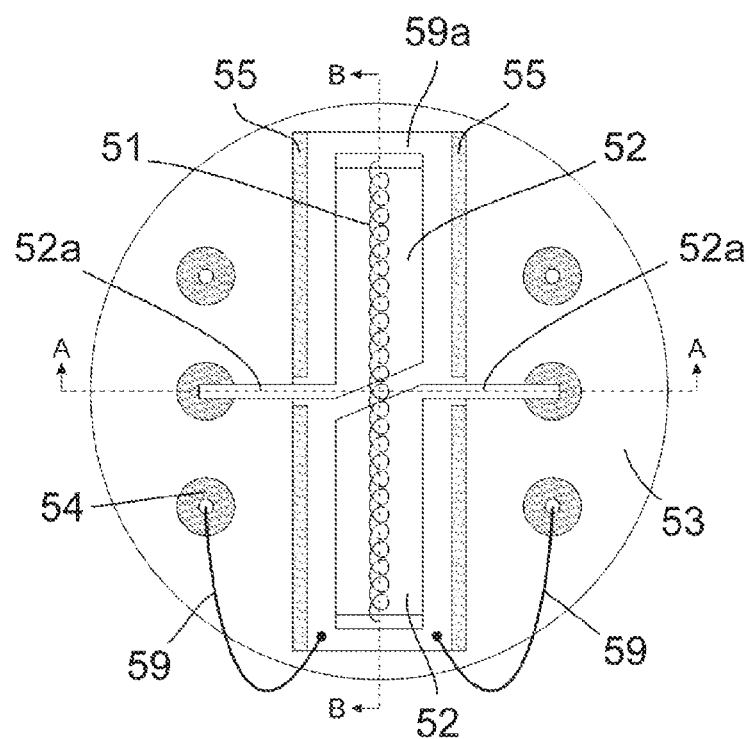
FIG. 5A is a top sectional view of an alternative Pirani sensor with a suspension heating element for loss compensation showing a filament measuring element.
Figure 5B:
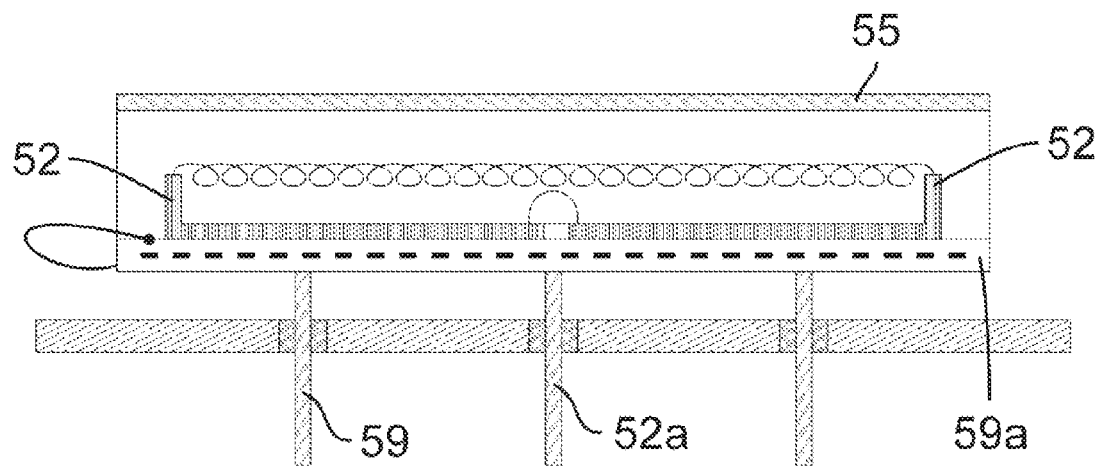
FIG. 5B is a side sectional view B-B of the sensor as in FIG. 5A.
Figure 5C:
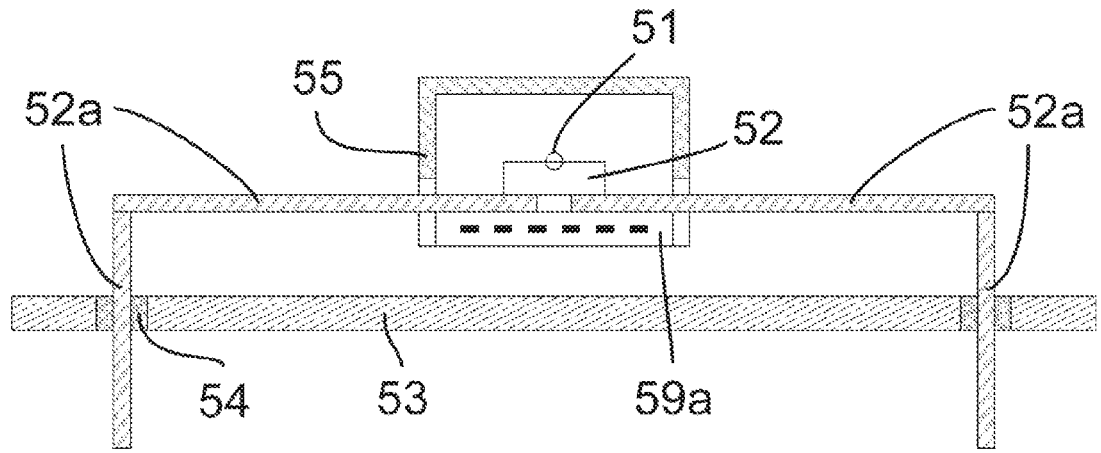
FIG. 5C is a front sectional view A-A of the sensor as in FIG. 5A.

FIGS. 5A-C show an alternative embodiment of a Pirani sensor with heat loss compensation. Here, a measuring element 51 is suspended by two suspension members 52. Each suspension member 52 comprises a band-shaped body, which is arranged in a plane parallel to the base plate 53 of the sensor. One end of the band-shaped body is bent upward. The measuring element 51 is attached to the upwardly facing end of the suspension member and extends above and substantially in parallel with the band-shaped body. The opposite end of the band-shaped body extends sideways into a narrow electrical lead 52a, which is bent downward to reach through bushings 54 in the base plate 53. A mirrored suspension member 52 connects the opposite end of the measuring element 51. The band-shaped body of both suspension members 52 is thermally conductively connected on top of a heating element 59a. A heat sink 55 is also thermally conductively connected to heating element 59a. As shown, the heat sink 55 comprises a substantially U-shaped cross section. The top of heat sink 55 extends substantially in parallel to heating element 59a. The sides of heat sink 55 extend downwardly onto heating element 59a, creating a tunnel in the center of which measuring element 51 extends axially. The heating element 59a is electrically connected to terminals 59 which reach through bushings 54 in the base plate 53. For operation this embodiment requires the measuring element 51 to at least in intervals assume a temperature above the temperature of the suspension members 52. Suspension heat loss does occur in this embodiment. However, due to the controlled temperature of the suspension members 52 and the heat sink 55 the suspension losses are constant and hence easier to discern from the heat transfer through the fluid than in traditional sensors.

Figure 5D:
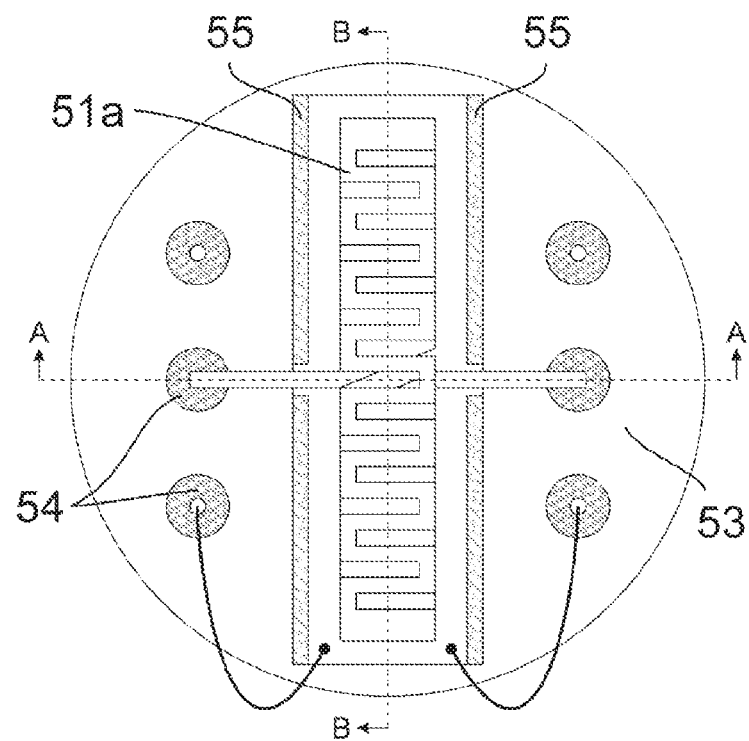
FIG. 5D is a top sectional view of an alternative Pirani sensor with a suspension heating element for loss compensation showing a meander-shaped measuring element.
Figure 5E:
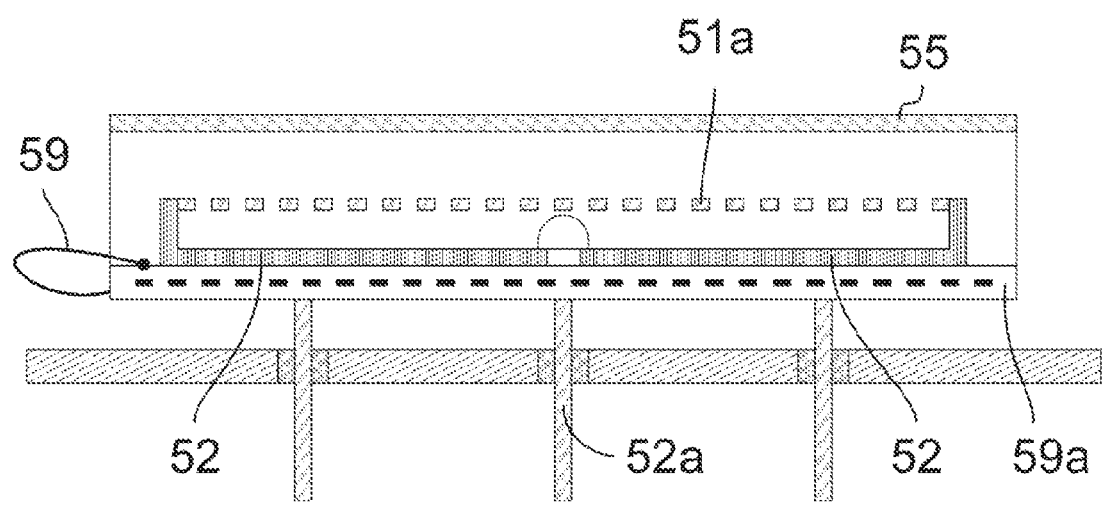
FIG. 5E is a side sectional view B-B of the sensor as in FIG. 5D.
Figure 5F:
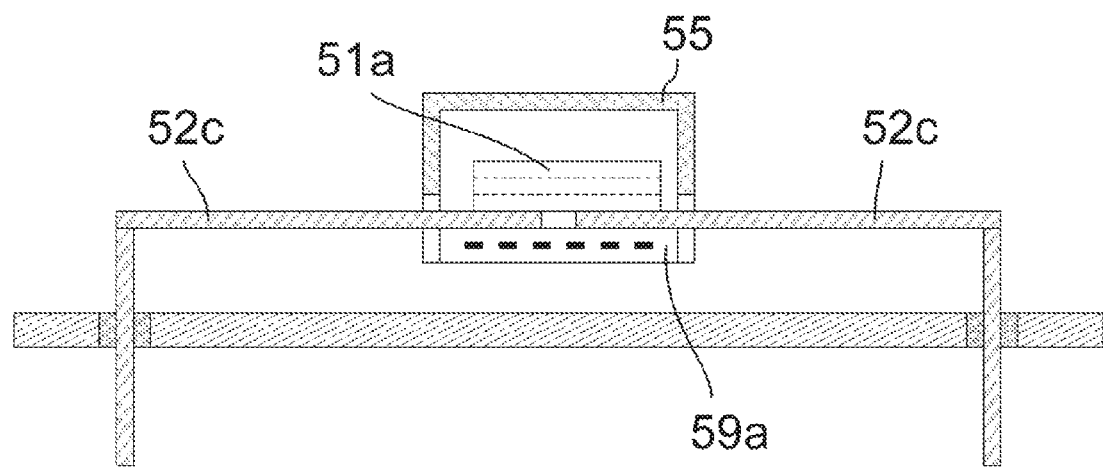
FIG. 5F is a front sectional view A-A of the sensor as in FIG. 5D.

FIGS. 5D-F show an alternative embodiment of a Pirani sensor with heat loss compensation. Here, the measuring element 51a is formed as a meander-shaped foil. The foil is made of suitable material, for example nickel, hard nickel or stainless steel.

Figure 5G:
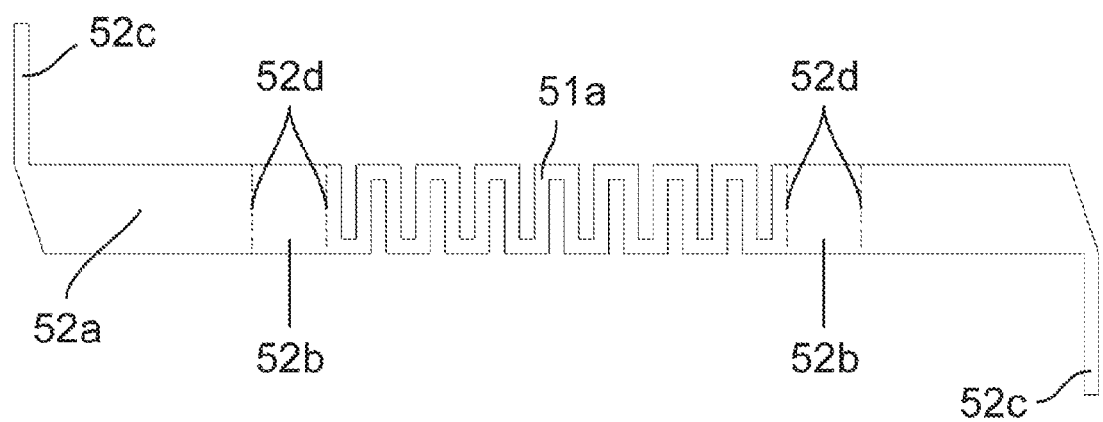
FIG. 5G is a detailed view of a meander-shaped measuring element.

FIG. 5G shows the metal foil used in the Pirani sensor of FIGS. 5D-F in more detail. As shown, the measuring element 51a and its electrical terminals are formed by cutting and bending from a single piece of foil. The foil comprises a central meandering section which serves as the measuring element 51a. Vertical sections 52b provide vertical spacing for the measuring element 51a and are bent approximately 90° downward from the central meandering section along a bending line 52d. Bent along a second bending line 52d the body sections 52a extend parallel to the meandering section inward. Extending outwardly from the body sections are electrical lead sections 52c. The ends of electrical lead sections 52c are bent downward to form electrical terminals which reach through bushings 54 in the base plate. The body sections 52a of this design a thermally conductively connected to the heating element 59a.

Figure 6A:
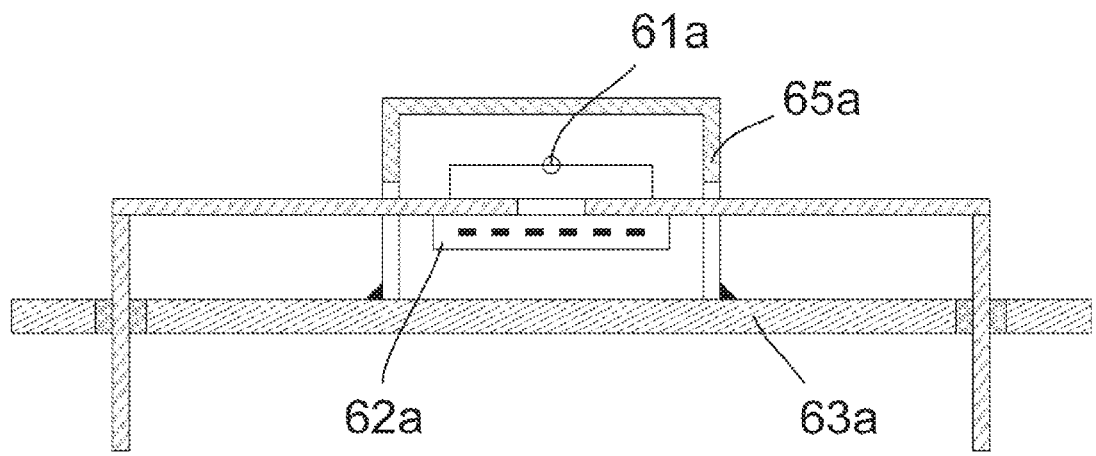
FIG. 6A is a front sectional view of an alternative Pirani sensor with a cover thermally conductively connected to a base plate.

An alternative design of the Pirani sensor as generally shown in FIG. 5 is illustrated in FIG. 6A. A heat sink 65a is thermally conductively connected to a base plate 63a. Both heat sink 65a and base plate 63a will normally assume ambient temperature. The measuring element 61a may be a filament such as shown in FIG. 5A-C or a flat measuring element as shown in FIGS. 5D-G.

Figure 6B:
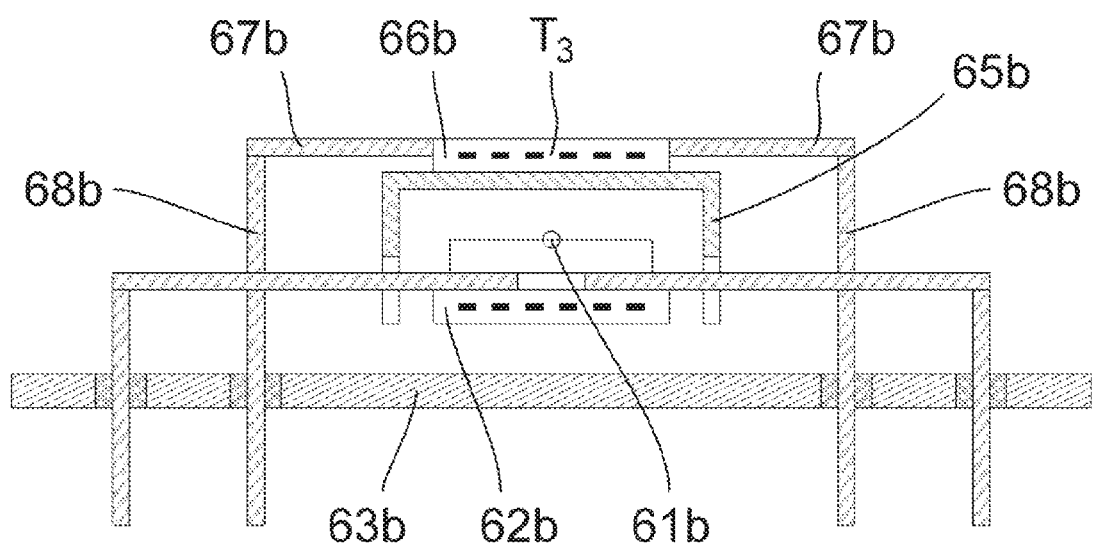
FIG. 6B is a front sectional view of an alternative Pirani sensor with a suspension heating element and a heat sink heating element.

FIG. 6B shows an alternative sensor with two heating elements. A suspension heating element 62b is provided underneath the measuring element 61b as shown before. A heat sink heating element 66b is provided above the measuring element 61b and thermally conductively connected to the heat sink 65b. The heat sink heating element 66b is held by the cover 67b. This allows control of the temperature of the heat sink 65b independently of the temperature of the suspension heating element 62b. The heat sink heating element 66b is connected by connection wires 67b to pins 68b which reach through bushings in the base plate 63b.

Figure 6C:
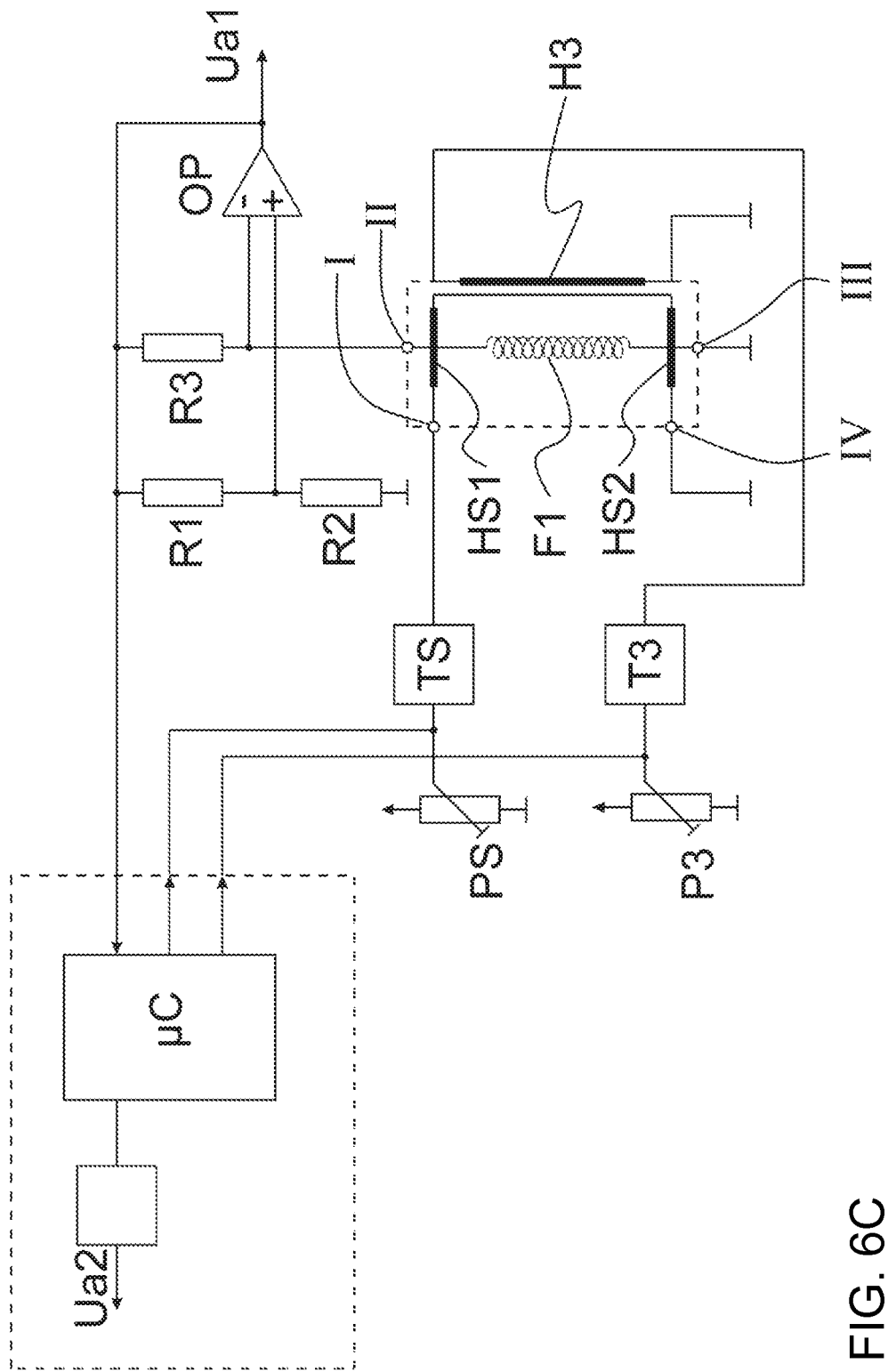
FIG. 6C shows an electronic circuit for operating a Pirani sensor with heat loss compensation in continuous mode.

FIG. 6C illustrates an electronic circuit suitable for connecting a sensor as in FIG. 6B. The measuring element F1 is connected within a Wheatstone bridge circuit with resistors R1, R2 and R3. Preferably, the Wheatstone bridge is symmetrical with R1=R2. The voltage across the bridge is amplifier by an operational amplifier OP to level $U_{a1}$ and fed into a control processor µC. $U_{a1}$ is a measure of the heat loss in the measuring element F1, and can be used to derive a fluid characteristic such as fluid vacuum pressure by further processing in the control processor. Two heating element HS1 and HS2 are provided to compensate heat losses in the suspension elements. As shown, heating elements HS1 and HS2 are connected in series to a suspension temperature controller TS. The suspension temperature controller TS is operatively connected to the control processor µC or to a potentiometer PS. The potentiometer PS is used to calibrate the target temperature of the suspension heating elements HS1 and HS2. This may be done during initial calibration after production of the sensor. To calibrate the sensor it is put in a vacuum, preferably of less than $10^{-5}$ mbar, e.g. at $10^{-7}$ mbar. The potentiometer PS, or alternatively the control processor µC output which is connected to suspension temperature controller TS, is adjusted until amplifier voltage across the bridge Ua1 is near zero.

A heat sink heating element H3 is provided and operatively connected to a heat sink temperature controller T3. The heat sink target temperature is selected either by adjusting potentiometer P3 or electronically controlled by the control processor µC, which is operatively connected to the heat sink temperature controller T3.

The circuit as shown in FIG. 6C resembles a four-terminal sensing circuit for measuring electrical impedance. To improve the accuracy of measuring the impedance of the measuring element F1 it is connected through terminals II and III, while heating elements HS1 and HS2 are separately connected through terminals I and IV. This allows reducing the current through the measuring element, and hence improving the accuracy of its measurement.

Figure 6D:
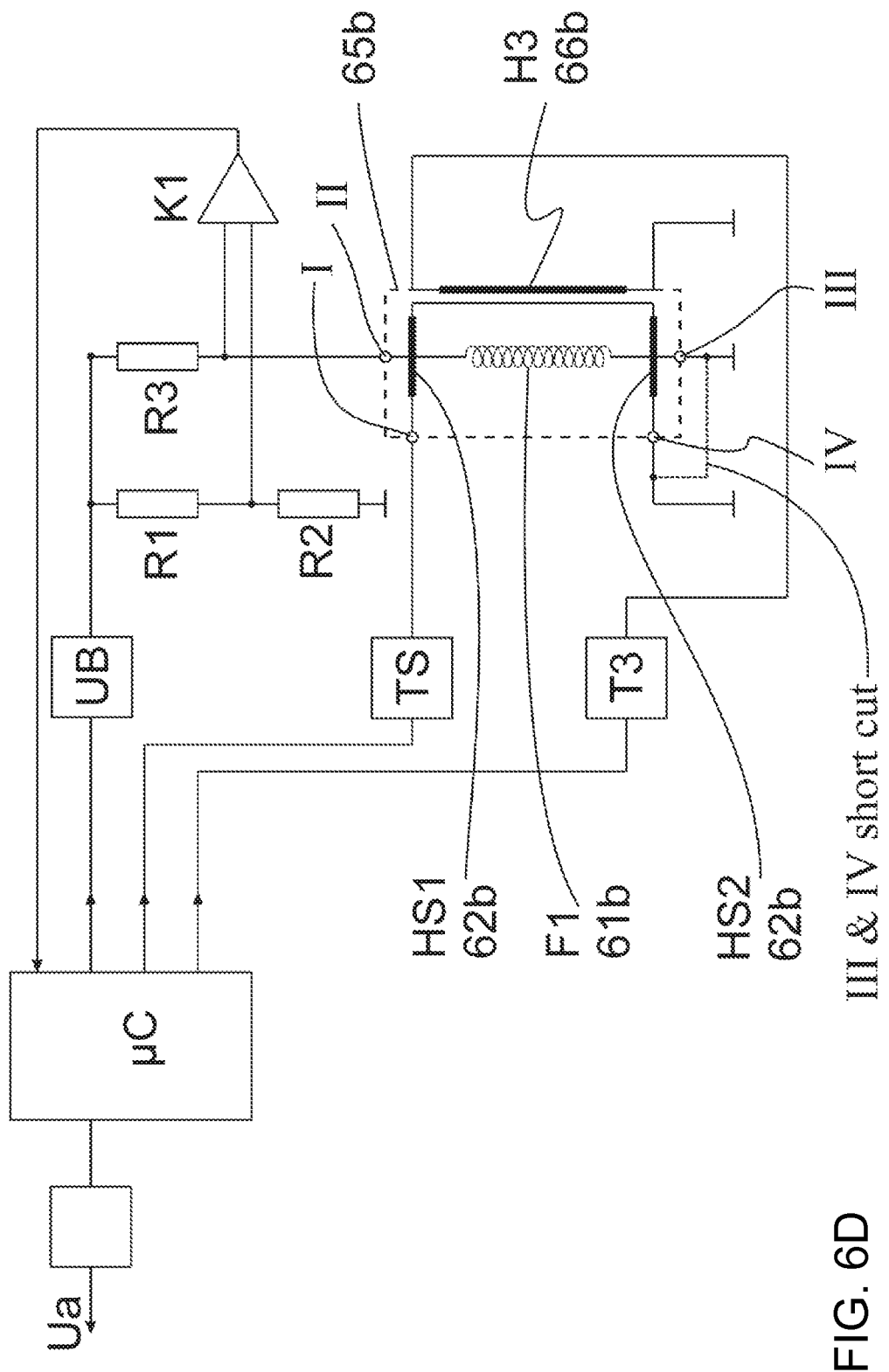
FIG. 6D shows an alternative electronic circuit for operating a Pirani sensor with heat loss compensation in continuous mode.

FIG. 6D illustrates an electronic circuit suitable for connecting a sensor as in FIG. 6B. In contrast to the circuit provided in FIG. 6D, sensor calibration in this example is automatically controlled through the control processor μC without manual adjustment of potentiometers. In this circuit, the measuring element F1 is within a Wheatstone bridge with resistors R1, R2 and R3. The Wheatstone bridge is powered by a variable voltage driver UB, which is operatively connected to and controlled by the control processor μC. The voltage across the bridge is fed into a comparator K1. The control processor μC adjusts the variable voltage driver UB until the comparator K1 flips. The level of UB at which the comparator K1 flips is processed in the control processor to derive a fluid characteristic of interest.

When used as a vacuum sensor, calibration is achieved by placing the sensor with the measuring element F1 (element 61b in FIG. 6B), the suspension heating elements HS1 and HS2 (elements 62b in FIG. 6B) and the heat sink heating element H3 (element 66b in FIG. 6B) into a vacuum, preferably of less than $10^{-5}$ mbar, e.g. at $10^{-7}$ mbar. During calibration the control processor μC controls the variable voltage driver UB to a low value which is just sufficient to create a voltage across the Wheatstone bridge and bias the comparator K1, but small enough not to heat the measuring element F1. The control processor then increases the suspension temperature by adjusting suspension temperature control TS until comparator K1 flips. The value to which TS was controlled when the comparator K1 flipped is stored in a non-volatile memory within the control processor μC.

The disclosed circuit also allows the control processor μC to control the temperature of a heat sink 65b through a heat sink heating element H3. The temperature of the heat sink can be independently controlled by the heat sink temperature controller T3 which is operatively connected to and controlled by the control processor. As shown, the return path IV of suspension heating elements HS1 and HS2 may be combined with the return path III of the measuring element F1.

Figure 7A:
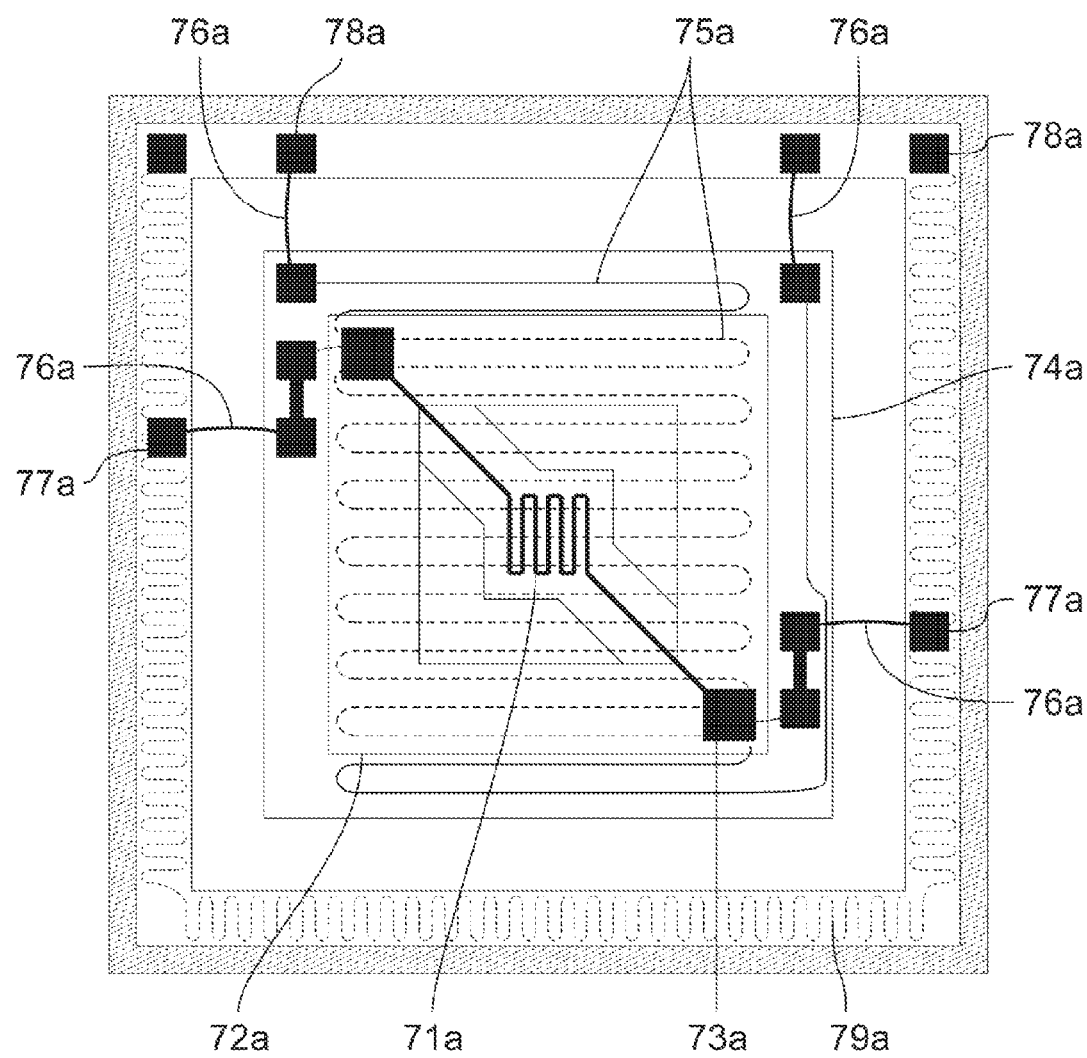
FIG. 7A is a top sectional view of a micro-Pirani sensor mounted onto a heating element.
Figure 7B:
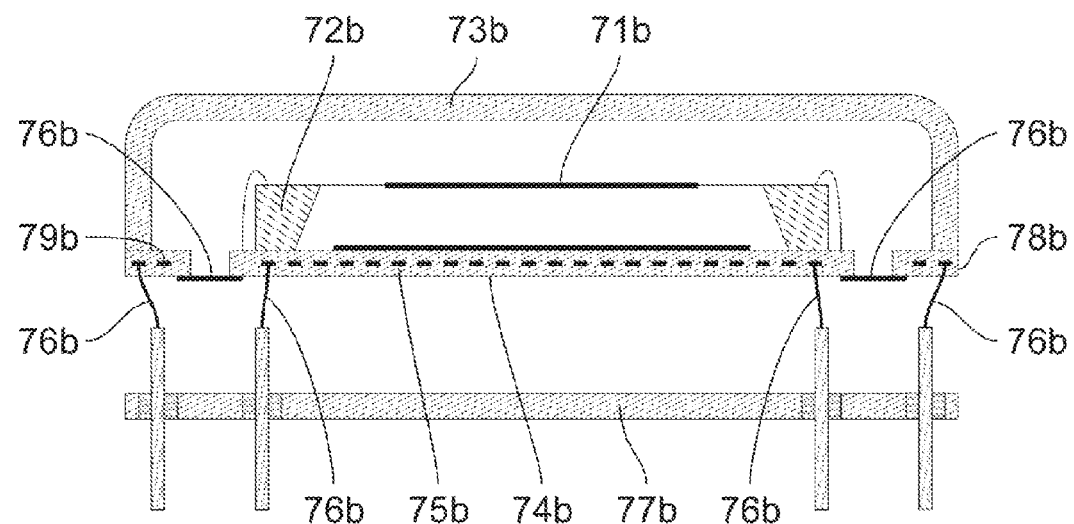
FIG. 7B is a side sectional view of the micro-Pirani sensor as in FIG. 7A.

FIGS. 7A-C and FIG. 8 show various micro-Pirani sensors, mounted onto heating elements for suspension heat loss compensating. More specifically, FIG. 7A and FIG. 7B show a micro-Pirani chip 72a with a measuring element 71a and bonding pads 73a. The chip 72a is mounted on a base plate 74a, which can be temperature controlled by means of a suspension heating element 75a. A cover 73b, which acts as a heat sink, is mounted onto a supporting frame 78a. A cover heating element 79a is provided underneath the supporting frame 78a. The measuring element 71a, the first suspension element 75a and cover heating element 79a are all electrically connectable from outside of the sensor. For the connection of the measuring element 71a, the contact surfaces 77a may be connected directly via bonding wires with the bonding pad 73a. A free standing mounting of the base plate 74a with the micro-Pirani chip 72a allows heating the base plate 74a and micro-Pirani chip 72a to a temperature generally above the ambient temperature with relatively low heating power.

FIG. 7B shows a side sectional view through a sensor as generally depicted in FIG. 7A. As illustrated, a suspension heating element 75b, which may be a resistive wire, is embedded within a base plate 74b. A measuring element 71b is connected to a chip 72b, which in turn is mounted onto the base plate 74b. A cover heating element 79b is embedded into a supporting frame 78b. A cover 73b is thermally conductively attached to the supporting frame 78b. The supporting frame 78b is freestanding on pins 76b, spatially separated above a carrier plate 77b. The pins 76b protrude the carrier plate 77b and allow connecting an electronic circuit to the measuring element 71b, to the suspension heating element 75b, and the cover heating element 79b.

This design allows controlling the temperature of the measuring element 71b to be the same as the temperature of the base plate 74b, thereby providing compensation of the suspension heat loss. Simultaneously, the cover 73b, which exchanges heat with the measuring element 71b through radiation, may be controlled to a second temperature to contain the radiation heat loss to a constant and predictable value. To further reduce the radiation heat losses the measuring element facing surface of the base plate 73b and the inner surface of the cover 73b may be reflectively coated.

Figure 7C:
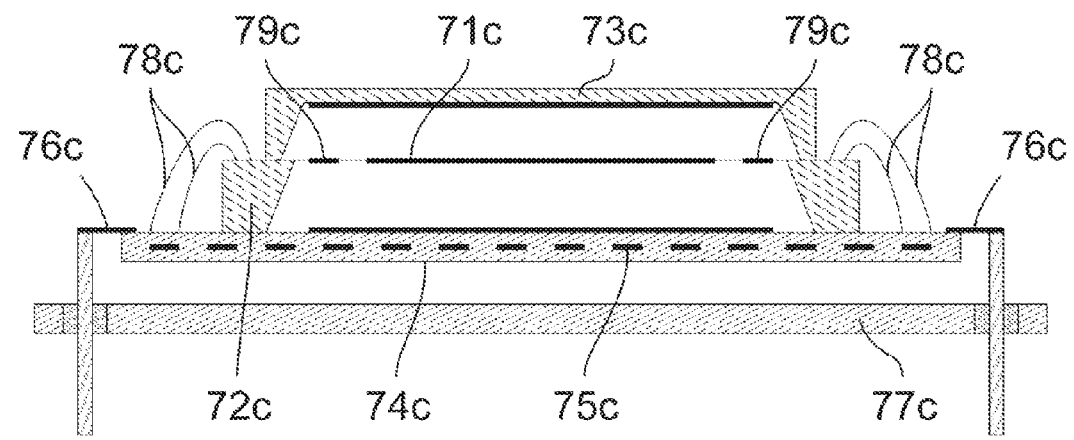
FIG. 7C is a side sectional view of an alternative micro-Pirani sensor with heat loss compensation.

FIG. 7C shows a cross sectional view of an alternative Pirani sensor. Here again, a membrane measuring element 71c is connected to a first chip 72c, which in turn is mounted onto a base plate 74c. Suspension heating elements 79c are disposed on the membrane between the measuring element 71c and the suspension points of the membrane to the first chip 72c. The suspension heating elements 79c and the measuring element 71c are electrically connected by bond wires 78c from the chip 72c to base plate 74c. Stacked onto the first chip 72c is a second chip 73c which serves as a cover and heat exchange surface. Embedded into the base plate 74c is a second heater element 75c. Through lead wires 76c, the base plate 74c is connected to contact pins of carrier plate 77c.

The suspension heating elements 79c are configured to compensate conductive suspension heat loss from the measuring element 71c into the first chip 72c. The inner surface of the cover 73c and the chip-bearing surface of the base plate 74c may be reflectively coated or metallized, in order to minimize radiation losses.

Figure 8:
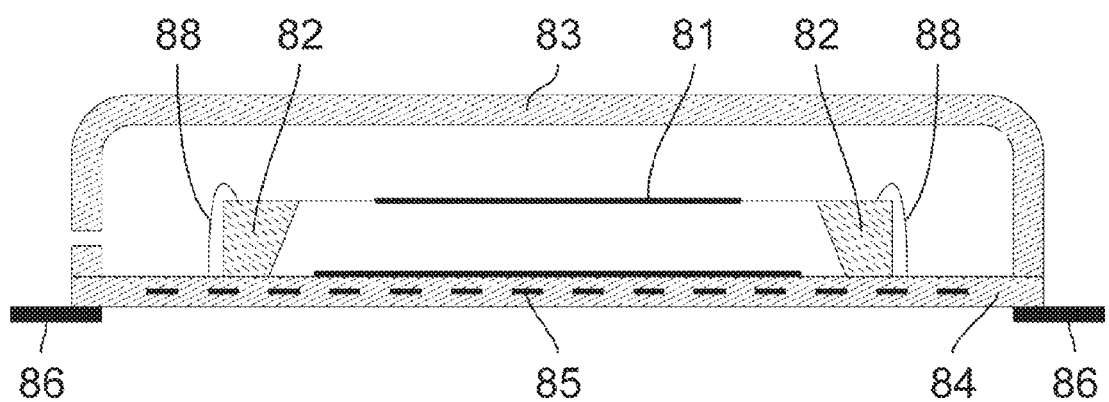
FIG. 8 is a cross sectional view of an alternative micro-Pirani sensor with a suspension heating element.

FIG. 8 is a sectional view of yet another variation of a micro-Pirani sensor with heat loss compensation. A micro-chip Pirani 82 carries a sensing element 81. The micro-chip Pirani 82 is mounted on a base plate 84. Embedded into the base plate 84 is a heat sink heater 85. The heat sink heater 85 is used to hold the base plate 84 at a constant temperature. A heat sink 83 is thermally conductively attached to the base plate 84, and hence assumes the same temperature as the base plate 84. Optionally, the inner surface of the heat sink 83 and the chip-bearing surface of the base plate 84 can be reflectively coated in order to minimize radiation losses. Since the base plate 84, the measuring element 81, and the heat sink 83 are at the same temperature, this structure is preferably operated with pulsed operating method.

The micro-chip Pirani 82 with the measuring element 81 is connected through bonding wires 88 to the base plate 84. Via connecting wires 86 that are attached to a pad 87, the measuring unit can be incorporated into a sensor assembly. For example, the disclosed micro-chip Pirani sensor may be combined with diaphragm pressure sensors, cold cathode vacuum sensors, or hot cathode vacuum sensors.

Figure 9A:
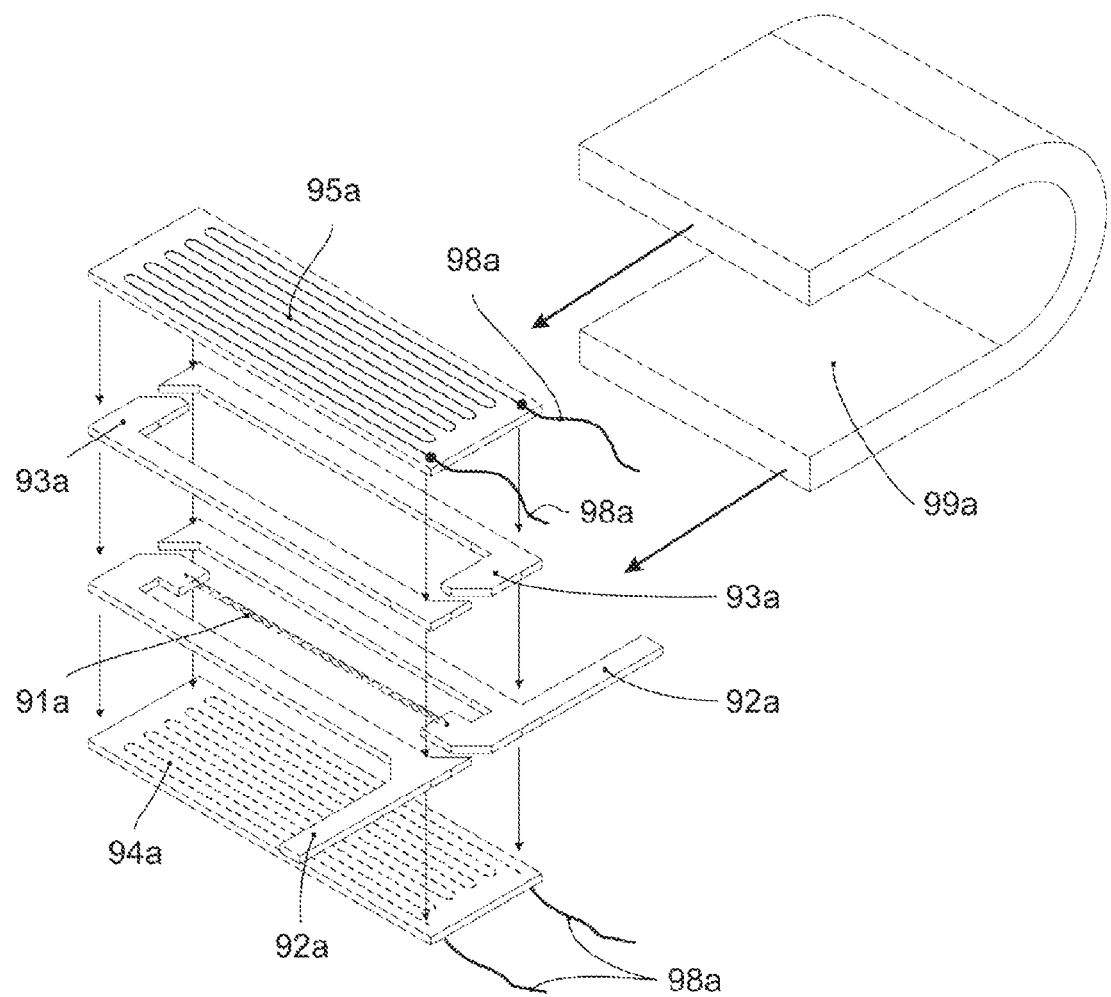
FIG. 9A is an exploded view a Pirani sensor with heating element enclosed by a metal bracket.
Figure 9B:
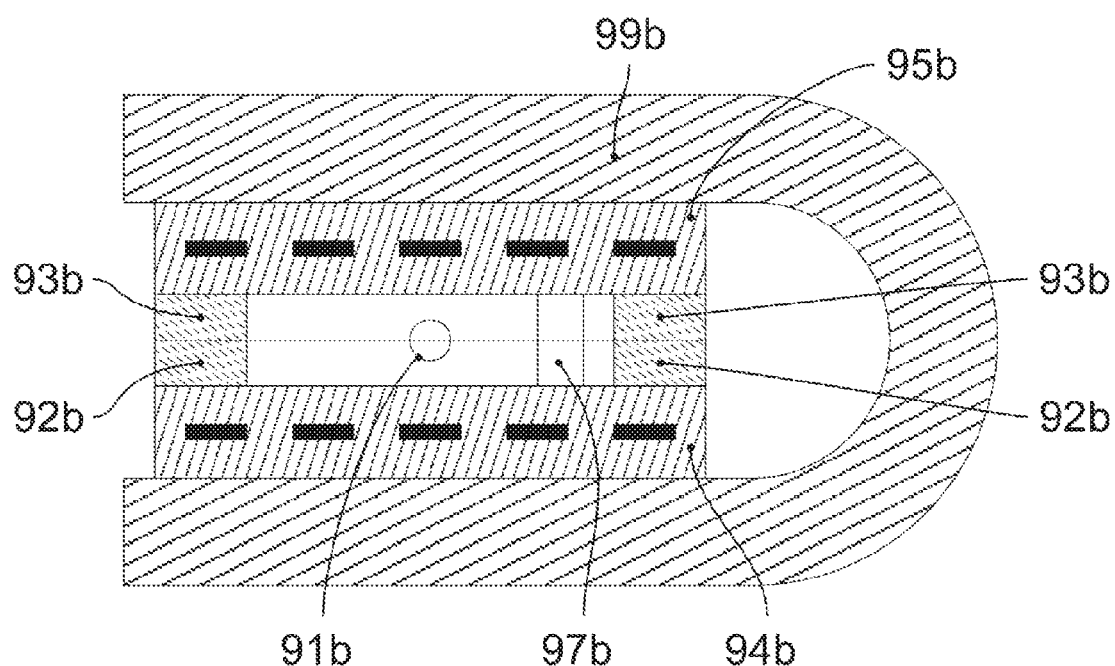
FIG. 9B is a cross sectional view of the Pirani sensor in FIG. 9A.

Referring now to FIG. 9A and FIG. 9B a Pirani sensor with heating element enclosed by a metal bracket is shown. The measuring element 91a is shown as a filament, but may also be implemented as a flat meander-shaped foil. The measuring element 91a is attached to suspension elements 92a, which dual-function as electrical terminals for electrically connecting the measuring element 91. Spacer pieces 93a are disposed above the suspension elements 92a and separate the suspension elements from an upper ceramic heating element 95a above. A lower ceramic heating element 94a is disposed below the suspension elements 92a. The upper and the lower ceramic heating elements 95a, 94a are connected by electrical wire leads 98a.

The lower ceramic heating element 94a, the suspension members 92a, the spacer pieces 93a and the upper ceramic heating element 95a are sandwiched together and held in place by a metal bracket 99a. The metal bracket 99a may for example be made of copper and hence be highly thermally conductive to ensure a uniform temperature across the sandwich structure.

Since the suspension members 92a are at the same temperature with the measuring element 91a and the upper and lower ceramic heating elements 94a, 95a, this structure is preferably operated with a pulsed method. As shown in FIG. 9B, fluid, that is a gas or liquid which is to be measured, can enter and exit the area around the measuring element 91a through a media inlet slot 97b.

Figure 12:
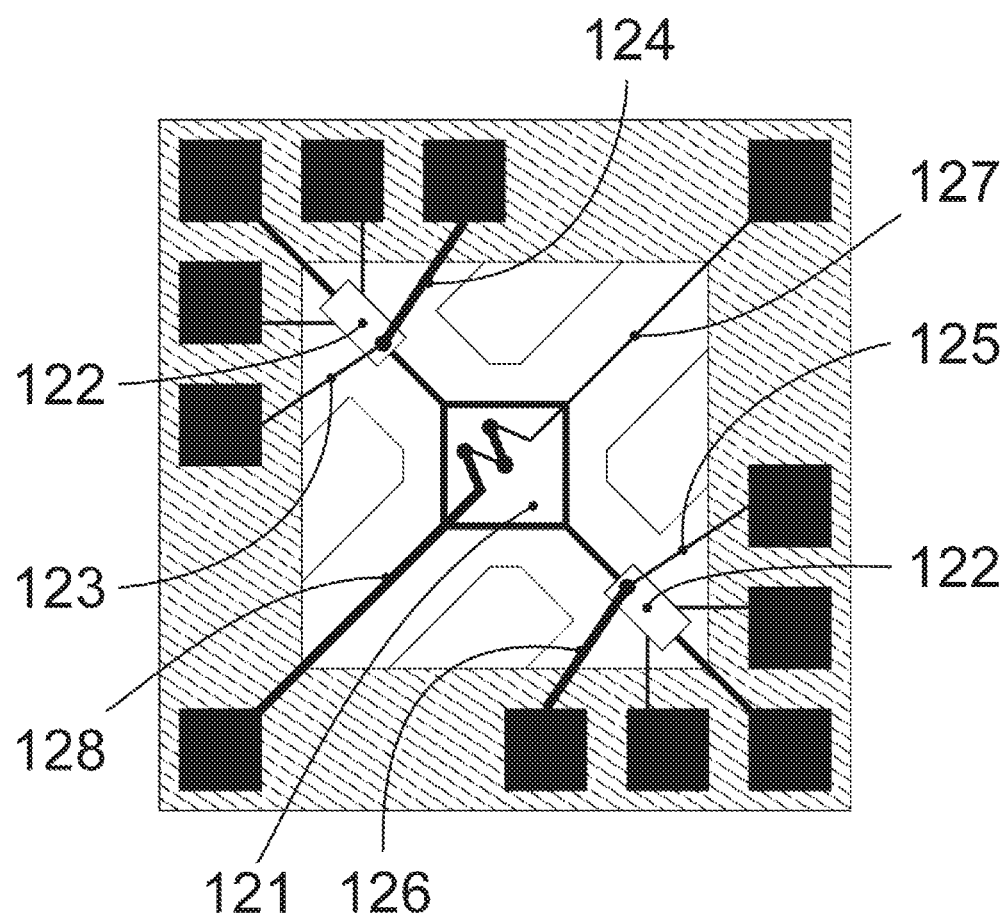
FIG. 12 shows a top view of a micro-Pirani sensor chip.

FIG. 12 shows the top view of a micro-Pirani sensor with a measuring element 121. Heating elements 122 are disposed on a membrane between the measuring element 121 and the suspension points of the membrane to the surrounding microchip. The heating elements 122 compensate for suspension heat loss.

An insulating layer, preferably an oxide layer with good thermal conduction, is disposed above both the sensor element 121 and the heating elements 122. Thermopile or thermocouple elements are disposed on this insulating layer. A first set of thermocouples 123/124, 125/126 (or one thermopile with n thermocouples) is positioned above the heating elements 122. A second set of two thermocouples 127/128 (or one thermopile with 2n thermocouples) is located above the measuring element 121. The connecting legs of the thermocouples on the membrane suspensions are lead out to connection pads on the chip.

If the heating elements 122 are at a higher temperature than the surrounding chip, the first set of two thermocouples 123/124, 125/126 will generate a first thermal voltage corresponding to the temperature difference between heating elements 122 and surrounding chip. If the measuring element 121 is at a higher temperature than the surrounding chip, the second set of two thermocouples 127/128 will generate a second thermal voltage corresponding to the temperature difference between measuring element 121 and surrounding chip.

If the chip is at ambient temperature, control of the measuring element temperature and the temperature of the suspension can take place in a simple manner to achieve a fixed distance from the ambient temperature by an electronic controller which compares the thermocouple voltage with a fixed voltage reference.

The thermocouples 123/124 may be wired in series with the thermocouples 125/126, and their combined thermal voltage and compared with the thermal voltage of the two thermocouples 127/128. When the measuring element 121 and the suspensions have the same temperature, the difference of the thermal voltages is equal to zero. The temperature of the measuring element 121, which is the same as that of the suspensions, can in a simple manner be kept at a fixed offset from the ambient temperature as a cascade control.

Operating Methods

Different methods can be used to operate the sensors according to the aforementioned embodiments.

Method 1:

| Element | Temperature/Control |
| --- | --- |
| Measuring Element | Controlled to substantially constant temperature $T_1$ |
| Measuring Element Suspension | Controlled to substantially constant temperature $T_1$ |
| Cover (Heat Exchange Surface) | Uncontrolled ambient temperature $T_A$. May optionally be measured by a temperature sensor. |

A sensor operating according to this method may be calibrated in an ultra-high vacuum environment. Calibration may for example be achieved through use of a Wheatstone bridge, in which the measuring element is the unknown electrical resistance to be measured. One of the other three resistors may be adjusted until the bridge voltage is zero. Calibration may also be achieved by inserting a variable corrective voltage into the Wheatstone bridge by a control processor. The calibration is saved for future measurements and corrects for the radiation heat loss which occurs even in a complete vacuum.

Method 2:

| Element | Temperature/Control |
| --- | --- |
| Measuring Element | Controlled by pulses, alternating between a lower temperature $T_1$ and a higher temperature $T_2$ |
| Measuring Element Suspension | Controlled to substantially constant temperature $T_1$ |
| Cover (Heat Exchange Surface) | Uncontrolled ambient temperature $T_A$ |

During pulsed operation of the measuring element the heat capacity of the measured fluid influences the measured signal. See Heinz Plöchinger, 2002, "Fortschritt in der Vakuum-Messtechnik", *Vakuum in Forschung and Praxis*, vol. 14, no. 5, pp. 281-283, and W. Jitschin & S. Ludwig, 2004, "Dynamical behaviour of the Piranisensor", *Vacuum*, vol. 75, pp. 169-176

Method 3:

| Element | Temperature/Control |
| --- | --- |
| Measuring Element | Controlled to substantially constant temperature $T_1$ |
| Measuring Element Suspension | Controlled to substantially constant temperature $T_1$ |
| Cover (Heat Exchange Surface) | Controlled to substantially constant temperature $T_3$, with $T_3 < T_1$ |

This method may be implemented for example by the electronic circuit as in FIG. 6C.

Method 4:

| Element | Temperature/Control |
| --- | --- |
| Measuring Element | Controlled by pulses, alternating between a lower temperature $T_1$ and a higher temperature $T_2$ |
| Measuring Element Suspension | Controlled to substantially constant temperature $T_1$ |
| Cover (Heat Exchange Surface) | Controlled to substantially constant temperature $T_3$, with $T_3 < T_1$ |

Method 5:

| Element | Temperature/Control |
| --- | --- |
| Measuring Element | Controlled to substantially constant temperature $T_1$ |
| Measuring Element Suspension | Controlled to substantially constant temperature $T_3$, with $T_3 < T_1$ |
| Cover (Heat Exchange Surface) | Controlled to substantially constant temperature $T_3$, with $T_3 < T_1$ |

The operating according to method 5 leads to a constant and hence predictable suspension heat loss.

Method 6:

| Element | Temperature/Control |
| --- | --- |
| Measuring Element | Controlled by pulses, alternating between a lower temperature $T_1$ and a higher temperature $T_2$ |
| Measuring Element Suspension | Controlled to substantially constant temperature $T_3$, with $T_3 < T_1$ |
| Cover (Heat Exchange Surface) | Controlled to substantially constant temperature $T_3$, with $T_3 < T_1$ |

Method 7:

| Element | Temperature/Control |
| --- | --- |
| Measuring Element | Power is applied until a higher temperature $T_2$ is reached. Power is turned off thereafter, allowing measuring element to cool down to equilibrium state in which measuring element, suspension and cover are at the same temperature $T_3$. |
| Measuring Element Suspension | Controlled to constant temperature $T_3$, with $T_3 < T_2$ |
| Cover (Heat Exchange Surface) | Controlled to constant temperature $T_3$, with $T_3 < T_2$ |

Method 7 is based on temporarily achieving an equilibrium state A in which no heat transfer takes place in the sensor. During this equilibrium state A the measuring element is not powered and the measuring element suspension and cover are heated or cooled until measuring element, suspension and cover are all at the same temperature. The measuring element (optionally the suspensions of a micro-Pirani) is supplied with additional energy only in pulses. After removal of the corresponding amount of heat through the gas (and a constant amount of heat in each of the suspensions and the radiation), the equilibrium state is established again.

Method 8:

| Element | Temperature/Control |
| --- | --- |
| Measuring Element | Controlled by pulses. Power is applied until a higher temperature $T_2$ is reached. Cooling period is a predetermined time $t_w$. |
| Measuring Element Suspension | Controlled to constant temperature $T_3$, with $T_3 < T_2$ |
| Cover (Heat Exchange Surface) | Controlled to constant temperature $T_3$, with $T_3 < T_2$ |

Method 8 leads to the measuring element alternating between an intermediate temperature $T_m$ which is between $T_2$ and $T_3$. The measuring element is alternately heated until a target temperature $T_2$ is reached, and cools for a predetermined period of time. This is different from method 7, which waits to start a new measurement cycle until the equilibrium state A is reached. Here, a new measuring pulse starts after a fixed waiting time $t_w$.

Method 9:

| Element | Temperature/Control |
| --- | --- |
| Measuring Element | Controlled by pulses. Power is applied until a higher temperature $T_2$ is reached. Cooling period is a predetermined time $t_w$. |
| Measuring Element Suspension | Heated synchronously by pulses to match temperature of the measuring element. |
| Cover (Heat Exchange Surface) | Controlled to substantially constant temperature $T_3$, with $T_3 < T_2$ |

Method 9 applies primarily to sensors with low-mass, such as a micro-Pirani. Here the suspension can be synchronously heated with a ramp from $T_1$ to $T_2$, thereby reducing the influence of the base power and the zero pressure is further reduced.

Method 10 introduces an improvement of any of the previously described methods with pulsed measuring element operation (methods 2, 4, 6, 7, 8 and 9). In the previously described methods the measuring element is powered during a pulse according to a fixed curve, preferably a voltage which ramps up with a ramp angle α. According to method 10, the slope of the ramp, i.e. its ramp angle α, is adjustable. Adjustment of the ramp angle is preferably controlled by a control processor which is used to control the sensor anyway. Adjustment of the ramp angle allows operation of the sensor over a wider measuring range. A slow rising pulse that powers the measuring element, i.e. a small ramp angle α, provides sufficient resolution in the measurement time also at low pressure. At higher pressures the increased heat dissipation through the measured fluid requires more power, and hence a steeper rise ramp to reach the target temperature in a short measurement time. Information about the current measurement range can be derived from one or more previous heat-up and/or cooling time periods of the measuring element itself or be derived from the power requirement of the controlled heating of suspensions and heat sink.

Method 11 introduces an improvement over any of the previously described pulsed methods in that the target temperature $T_2$ to which the measuring element is heated during a pulse is adjustable.

According to method 12, both the slope of the rise ramp (angle α), as well as the target temperature T2 and the subsequent waiting time $t_w$ for the cooling period can be adjusted by the control processor in order to bake out the measuring element at a higher temperature and thereby eliminate contaminants adhering to the measuring element. Whether this cleaning process is necessary can be determined during the startup of the measuring element at atmospheric pressure by comparing the first heating time $t_{m0}$ from $T_1$ to $T_2$ with a value that is stored in the memory of the control processor, and that has been set during factory calibration. If the measuring element is contaminated, the first warm-up time $t_{m0}$ is longer than in the original state. This procedure "Measurement element check and bake-out" can optionally be executed by pressing a button or by an external command.

Where the disclosed methods refer to controlling a constant or constant temperature one skilled in the art will appreciate that no control is perfect, and hence "constant temperature" refers to a temperature that is at a substantially constant level within what is technically achievable. One skilled in the art will also appreciate that variations of the disclosed methods can achieve similar results. For example, where two temperature values are controlled, not both of them need be controlled to an absolute value. Rather, one may be controlled to maintain a predetermined temperature offset from the other. The temperature of the suspension elements may for example be maintained at a constant offset from the cover temperature. The cover temperature may be variable, e.g. uncontrolled at the ambient temperature, at an absolute temperature, at a predetermined offset from the ambient temperature, or even following a predetermined curve.

While the described sensors and methods are primarily intended to measure pressure of a gas, they can also be used for identification of a gas. A particular gas can be identified by pattern-matching if the heat conductivity and, optionally, the heat capacity of the respective gas depends on the temperature. The gas to be identified is exposed to a sensor at a constant pressure, for example at atmospheric pressure. Any of the methods above may be used to identify the gases heat capacity, which is compared with predetermined values stored in a lookup table.

FIG. 10A shows the temperature over time of a measuring element when operated in a pulsed mode. From an ambient temperature level, e.g. $T_{A2}$, the measuring element is heated to a controlled temperature level $T_{F1}$. $T_{F1}$ is the steady temperature to which the suspension is controlled. After a settling time a first pulse on the measuring element is started by the control processor at $t_0$. The voltage which is applied to the measuring element is illustrated in FIG. 10B. The power applied to the measuring element causes it to heat from $T_{F1}$ to $T_{F2}$. By measuring the temperature of the measuring element, and comparing it with a target value, the control processor stops the pulse at time $t_1$ when the measuring element has reached temperature $T_{F2}$.

The period of time $t_{m0}$ between $t_0$ and $t_1$ is essentially a measure for the amount of heat was lost by heat conduction through the measured fluid and thus a measure of the fluid pressure. If this time $t_{m0}$ recorded and stored for an individual brand new sensor, it can be used later as a reference for contamination of the sensor element.

If the cover of the sensor is at ambient temperature, e.g. $T_{A2}$, the cooling of the measuring element will take place according to the dashed curve $K_{a2}$. Dashed cooling curves $K_{a1}$, $K_{a3}$, and $K_{a4}$ respectively illustrate the cooling for alternative ambient temperatures $T_{A1}$, $T_{A3}$, and $T_{A4}$. However, when the cover temperature is also controlled to $T_{F1}$, a cooling curve A1 applies. Under high vacuum, the time taken to reach the point A1 is very long.

Provided a substantially constant temperature offset between $T_{F1}$ and $T_{F2}$, the cooling curve is always the same at a given pressure. The cooling curve of the de-energized measuring element can thus also be used in the measurement. In a simple way this is achieved in that after switching off at time $t_1$ the control processor waits a fixed predetermined waiting time $t_w$ until at the time $t_2$ a new pulse starts. The sensing element need not be cooled to the point A1. At the same pressure the new heating time $t_{m1}$ (between $t_2$ and $t_3$) of the measuring element will shorter than $t_{m0}$. This new heating time $t_{m1}$ not only contains information about the current heat loss by conduction through the fluid, but also depends on the previous cooling curve which crossed $t_2$ at the start of the new pulse.

At constant pressure, another pulse after a further waiting time $t_w$ at time $t_4$ will lead to the same heating time: $t_{m1}=t_{m2}$. Any subsequent heating time will be identical and referred to as $t_{mx}$. The time $t_{mx}$ as well as the corresponding frequency ($1/t_{mx}+t_w$) may serve as a measuring signal. A change in pressure of the fluid leads to a change in time $t_{mx}$ and of the corresponding frequency.

FIG. 10B shows a ramp pulse voltage over time with a pulse-rise angle α applied to the measuring element to generate heat pulses of the measuring element as in FIG. 10A.

FIG. 10C shows an alternative voltage pulse over time, to generate heat pulses generally as in FIG. 10A.

FIG. 11A shows the temperature over time of a measuring element when operated in a pulsed mode as in FIG. 10A, but using a different heating pulse shape. As illustrated in FIG. 11B the ramp angle of the voltage pulses applied to the measuring element have a smaller ramp angle α than those in FIG. 10B. Correspondingly, all else being equal, time periods $t_{m0}$ and $t_{mx}$ are extended. Generally, the lower a pulse-rise angle α, the better the time resolution at low pressures.

In addition to the rise angle α the target temperature $T_{F2}$ and the waiting time $t_w$ may also adjusted by the control processor to carry out a measuring range adaptation or eliminate dirt adhering to the measuring element.

If the temperature of the suspension, the temperature of the measuring element and the surface temperature of the heat sink are the same level $T_{F1}$, no heat flow takes place. From this equilibrium state power may be applied to the measuring element during a measuring cycle until the measuring element reaches a new constant temperature $T_{F2}$. Power may be applied in form of constant voltage, constant current, ramped voltage or ramped current. While the measuring element is at a temperature higher than the surrounding cover surface, heat is conducted through the fluid surrounding the measuring element into the heat sink. The amount of heat conducted through the fluid varies with the pressure of the fluid, and can hence be used to measure fluid pressure. Simultaneously heat losses through radiation and heat transfer into the suspension occur, but those depend on the known difference between $T_{F1}$ and $T_{F2}$, and are hence constant.

In case power is supplied according to a fixed characteristic curve (pulse, ramp) the initial heating time $t_{m0}$ from start at time $t_0$ and temperature $T_{F1}$ to stop at time $t_1$ and temperature $T_{F2}$ is a measure of the measured fluid variable, for example its pressure. After reaching temperature $T_{F2}$, the measuring element remains without power or with substantially reduced power and cools down to temperature $T_{F1}$. The cooling curve is again dependent only on the measured fluid variable and the temperature delta between $T_{F1}$ and $T_{F2}$.

With the same measured fluid variable, e.g. at constant fluid pressure, the cooling curve always has the same shape. Thus, not only the relationship between measured variable and heating curve, but also the relationship between measured variable and cooling curve can be used for measuring. The detection of an equilibrium state in which measuring element, suspension and cover are at the same temperature is theoretically possible, but practically difficult. Also, allowing the measuring element to cool down all the way to the cover temperature extends the measurement time, especially when the fluid pressure is low. It is hence more beneficial to not let the measurement element cool down completely, but rather apply a fixed cool down time period $t_w$. As of the second cycle $t_{m1}$ the sensor so operated automatically assumed a constant cycle frequency, which is a measure of the measured fluid variable and is largely independent of environmental influences.

If the offset between $T_{F1}$ and $T_{F2}$ is small, sufficiently short measurement times can be achieved. Losses through the suspensions and radiation are present, but they are minor and constant.

Figure 10D:
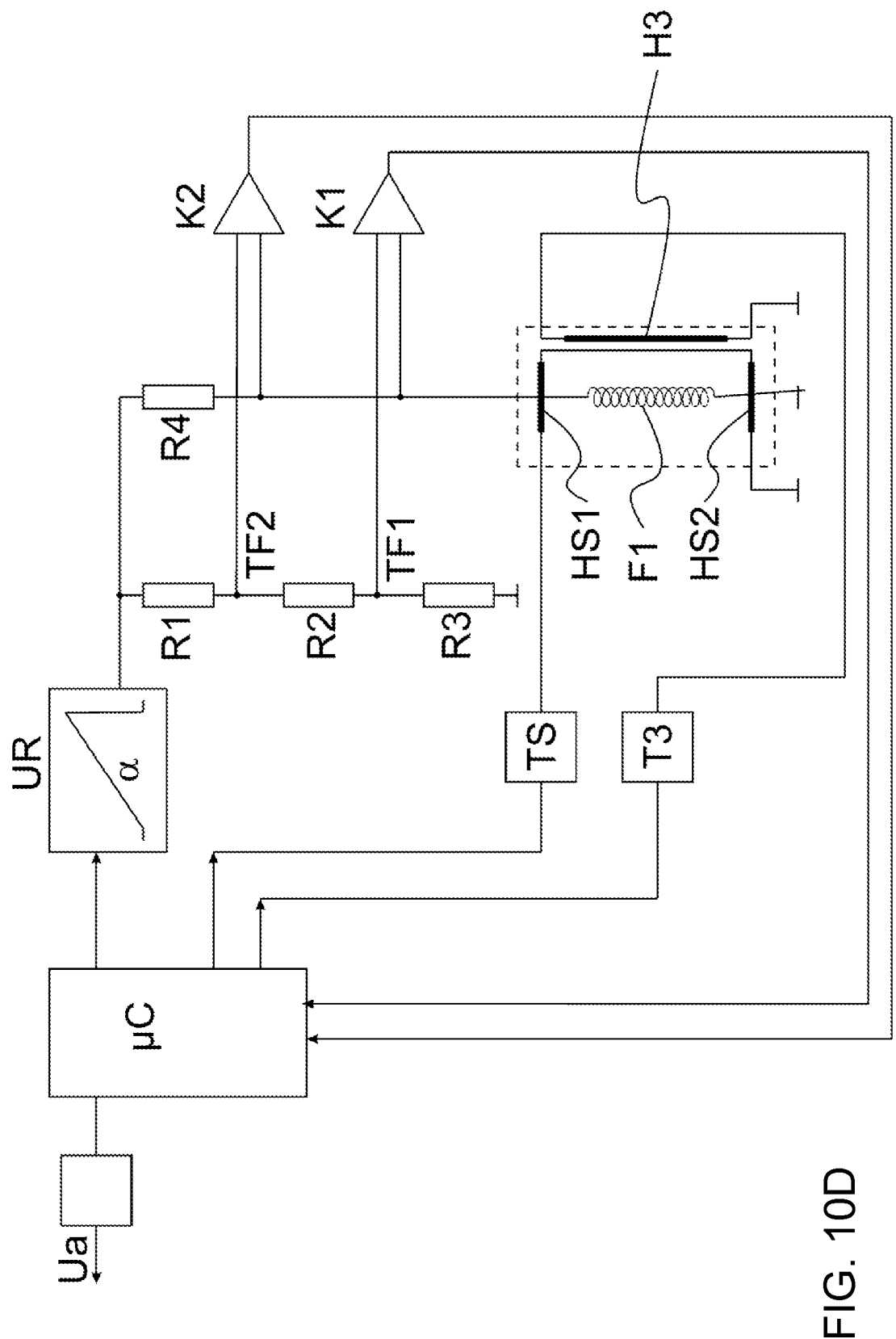
FIG. 10D shows an electronic circuit for operating a Pirani sensor with heat loss compensation in a pulsed mode.

FIG. 10D illustrates an electronic circuit suitable for connecting a sensor as in FIG. 6B and operating it in a pulsed mode as illustrated in FIG. 10A. The circuit here presented is based on the disclosure of a thermocouple vacuum gauge sensors in U.S. Pat. No. 8,047,711 by the same applicant which has been incorporated by reference. In contrast to the circuit provided in FIG. 6D, impedance of the measuring element F1 is evaluated by two separate comparators K1 and K2. The measuring element F1 forms a voltage divider with series resistor R4. The series connection of R4 and the measuring element are powered by a voltage ramp generator UR. Connected in parallel to R4 and the measuring element is a series of three resistors R1, R2 and R3. The voltage ramp generator UR is operatively connected to and controlled by a control processor μC. The impedance ratio of the measuring element F1/(F1+R4) is compared against a lower threshold R3/(R1+R2+R3) by a lower threshold comparator K1. The impedance ratio of the measuring element F1/(F1+R4) is also compared against an upper threshold (R2+R3)/(R1+R2+R3) by an upper threshold comparator K2. Both comparators are operatively connected to the control processor.

Since the temperature and impedance of the measuring element F1 are correlated, the lower threshold comparator K1 provides a signal to the control processor μC when the temperature of the measuring element F1 falls below a lower temperature threshold TF1. The upper threshold comparator K2 provides a signal when the temperature of the measuring element F1 rises above an upper temperature threshold TF2.

When used as a vacuum gauge, the pressure of the gas surrounding the measuring element F1 can be determined as described with reference to FIG. 10A before. After reaching the upper threshold temperature the control processor μC turns off voltage ramp generator UR. After a predetermined wait time $t_w$ the control processor enables voltage ramp generator UR and measures the time $t_x$ until K2 again indicates reaching the upper temperature threshold. The measure $t_x$ is indicative of the vacuum pressure and can be further processed by the control processor.

Calibration is achieved by placing the sensor into a vacuum, preferably of less than $10^{-5}$ mbar, e.g. at $10^{-7}$ mbar. During calibration the control processor μC controls voltage ramp generator UR to a low constant value which is sufficient to bias comparator K1, but small enough not to heat the measuring element F1. The control processor μC then increases the suspension temperature by adjusting the suspension temperature controller TS until the comparator K1 flips. The value to which the suspension temperature controller TS was controlled when the comparator K1 flipped is stored in a non-volatile memory within the control processor μC.

The control processor μC also controls the temperature of a heat sink disposed adjacent to the measuring element F1 by adjusting power to the heat sink heating element H3 through heat sink temperature controller T3.

Figure 10E:
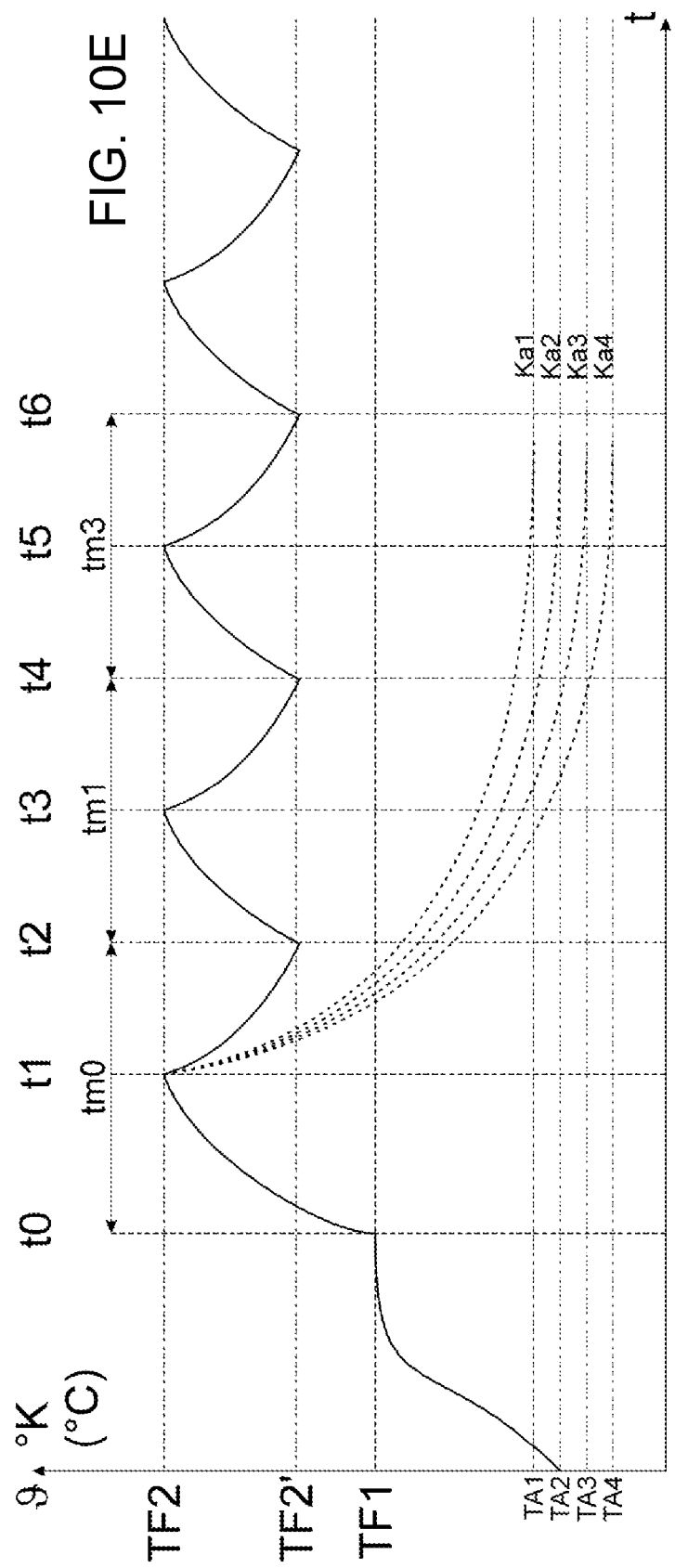
FIG. 10E is a diagram to illustrate temperature and voltage of a Pirani sensor over time when used in an electronic circuit as in FIG. 10F.
Figure 10F:
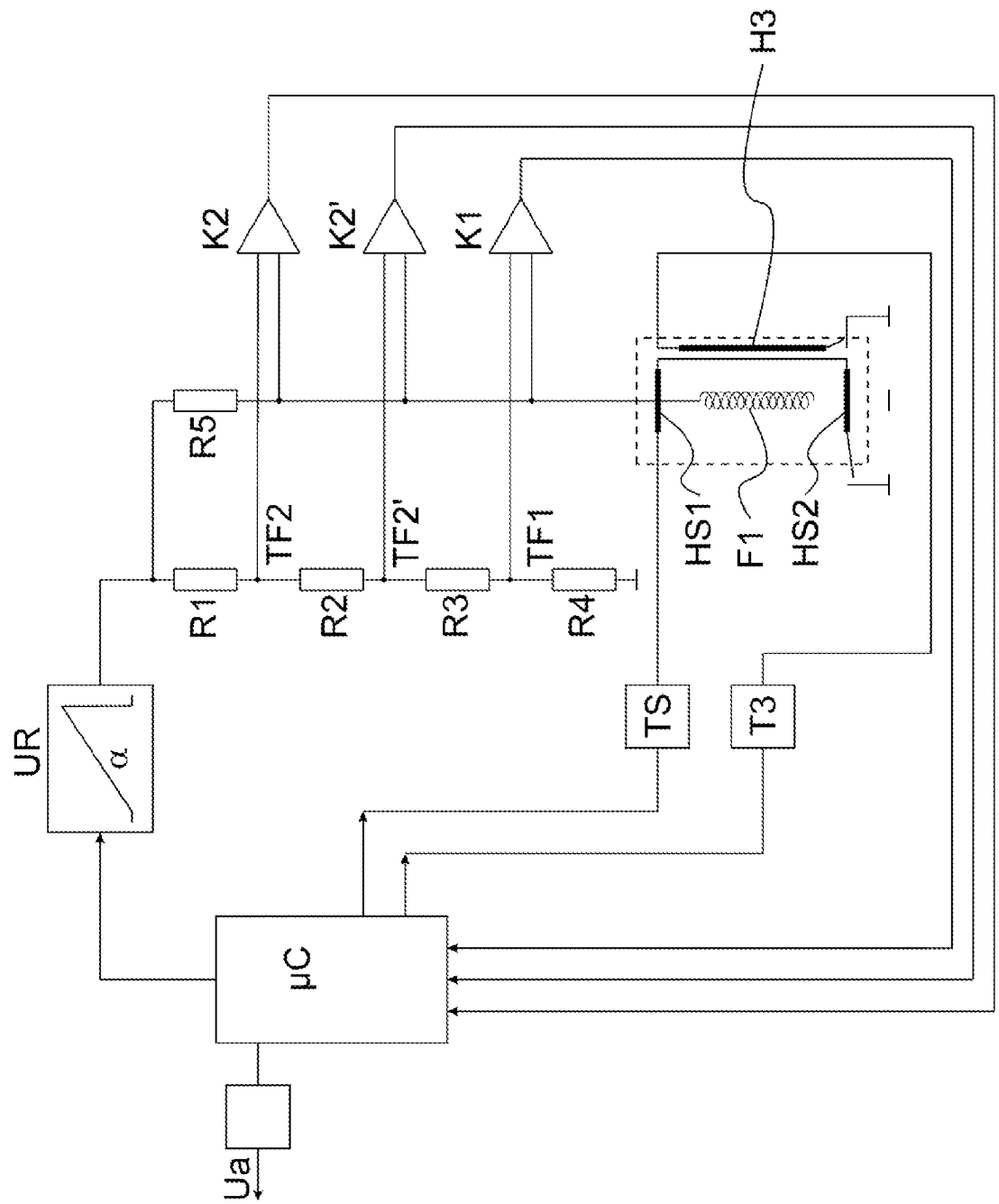
FIG. 10F shows an alternative electronic circuit for operating a Pirani sensor with heat loss compensation in a pulsed mode.

As illustrated in FIG. 10E, instead of applying a predetermined wait period $t_w$, the sensor may operate by alternating the measuring element temperature between an intermediate temperature threshold TF2' and an upper temperature threshold TF2. This is achieved by adding an additional intermediate temperature comparator K2' to the electronic circuit as illustrated in FIG. 10F. The control processor μC in this example activates the voltage ramp generator UR in response to an intermediate temperature threshold signal from the intermediate threshold comparator K2'. The control processor deactivates the voltage ramp generator UR in response to an upper temperature threshold signal received from upper threshold comparator K2.

Figure 13:
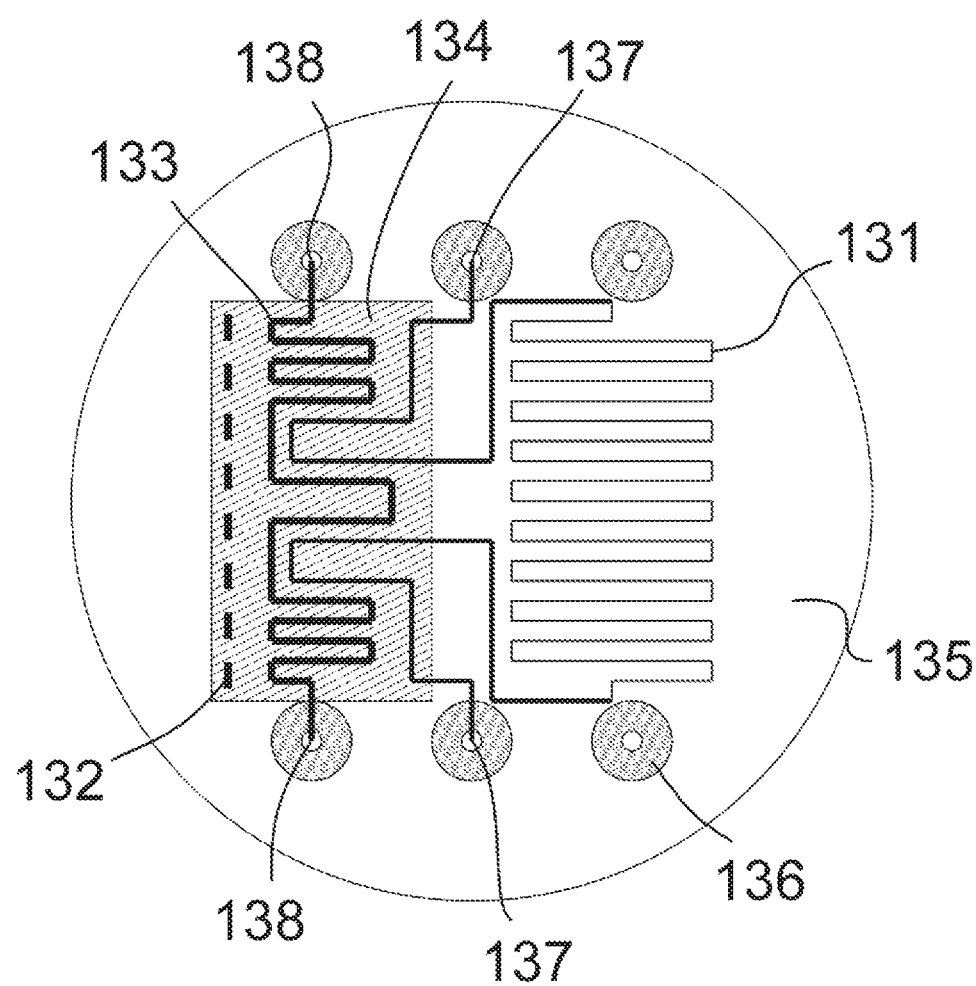
FIG. 13 shows a top view of a sensor chip with meander-shaped sensing and heating elements.

FIG. 13 shows an alternative sensor, in which measuring element 131 is a substantially flat meander-shaped wire or foil. The measuring element here extends sideways from a base plate 134 into the fluid and is connected to electrical terminals 137. The base plate 134 is heated by suspension heating element 133, which is a meander-shaped heating wire disposed in the same plane as the measuring element. The wires between the electrical terminals 137 to the measuring element 131 are thermally connected to the base plate 134 to pick up the applied compensation power from the heating element 131.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

What is claimed is:

1. A thermal conductivity sensor for measuring a characteristic of a fluid, comprising:
    a measuring element disposed within the fluid adjacent to a heat sink, the measuring element being held by suspension members;
    one or more suspension heating elements thermally conductively connected to the suspension members; and
    a control processor operatively connected to the measuring element and to the one or more suspension heating elements,
    wherein the one or more suspension heating elements are operatively connected to a suspension temperature controller, and
    wherein the control processor applies power to the one or more suspension heating elements to maintain a substantially constant temperature $T_1$, and
    wherein the control processor applies pulsed power to the measuring element until the measuring element reaches a predetermined temperature $T_2$.

2. The sensor as in claim 1, wherein the sensor is a Pirani sensor, the fluid is a gas, and the characteristic of the fluid is vacuum pressure.

3. The sensor as in claim 1, further comprising a heat sink heating element thermally conductively connected to the heat sink for maintaining a predetermined heat sink temperature.

4. The sensor as in claim 1, wherein the measuring element or the heat sink or both the measuring element and the heat sink comprise a reflective surface.

5. The sensor as in claim 1, further comprising a non-volatile memory, wherein the control processor controls the temperature of the one or more suspension heating elements depending on a calibration value stored in the non-volatile memory.

6. The sensor as in claim 1, further comprising a variable resistor, wherein the temperature of the one or more suspension heating elements is calibrated by changing the variable resistor.

7. The sensor as in claim 1, further comprising
an upper threshold comparator operatively connected to the control processor for detecting an upper temperature threshold of the measuring element,
wherein the control processor applies, through a variable voltage generator, power to the measuring element until a signal from the upper threshold comparator is received, and
wherein the control processor turns off or substantially reduces an output of the variable voltage generator for a predetermined time $t_w$ after the signal from the upper threshold comparator is received.

8. The sensor as in claim 1, further comprising
an upper threshold comparator operatively connected to the control processor for detecting an upper temperature threshold of the measuring element; and
an intermediate threshold comparator operatively connected to the control processor for detecting an intermediate temperature threshold of the measuring element,
wherein the control processor applies, through a variable voltage generator, power to the measuring element until a signal from the upper threshold comparator is received, and
wherein the control processor turns off or substantially reduces an output of the variable voltage generator until a signal from the intermediate threshold comparator is received.

9. A thermal conductivity sensor for measuring a characteristic of a fluid, comprising:
a measuring element disposed within the fluid adjacent to a heat sink, the measuring element being held by a first suspension member and a second suspension member,
a first suspension heating element thermally conductively connected to the first suspension member and a second suspension heating element thermally conductively connected to the second suspension member; and
a control processor operatively connected to the measuring element, to the first suspension heating element, and to the second suspension heating element,
wherein the control processor determines the characteristic of the fluid by evaluating heat transfer from the measuring element through the fluid into the heat sink when heating power is applied to the measuring element, and
wherein the control processor at least partially compensates parasitic conductive heat loss from the measuring element into the first suspension member and into the second suspension member is by applying compensation power to the first suspension heating element and to the second suspension heating element.

10. The sensor as in claim 9, wherein the first suspension heating element and the second suspension heating element are wired in series.

11. The sensor as in claim 9, wherein the first suspension heating element and the second suspension heating element are wired in parallel.

12. The sensor as in claim 1,
wherein the control processor determines the characteristic of the fluid by evaluating heat transfer from the measuring element through the fluid into the heat sink when heating power is applied to the measuring element, and
wherein the control processor at least partially compensates parasitic conductive heat loss from the measuring element into the suspension members by applying compensation power to the one or more suspension heating elements.

13. The sensor as in claim 12,
wherein the control processor evaluates the heat transfer from the measuring element into the fluid by measuring a time $t_x$ required to heat the measuring element from a first temperature $T_1$ to a second temperature $T_2$ and derives the characteristic of the fluid by calculating a measure from the time $t_x$.

14. The sensor as in claim 12,
wherein the control processor detects an upper temperature threshold of the measuring element, and
wherein the control processor applies measuring power to the measuring element during a heating phase until the measuring element reaches the upper temperature threshold.

15. The sensor as in claim 14,
wherein following the application of measuring power during the heating phase the control processor turns off or substantially reduces measuring power during a predetermined cooling phase wait period $t_w$, and
wherein the control processor uses at least one of the frequency $1/(t_x+t_w)$, the sum of tx+tw, and the ratio tx/tw to derive pressure of the fluid.

16. The sensor as in claim 14,
wherein the control processor detects an intermediate temperature threshold of the measuring element,
wherein following the application of measuring power during the heating phase the control processor turns off or substantially reduced measuring power during a cooling phase until the measuring element reaches the intermediate temperature threshold,
and wherein the control processor uses a duration of the heating phase or a duration of the cooling phase or a sum thereof to evaluate heat transfer from the measuring element into the fluid.

17. The sensor as in claim 14,
wherein the control processor applies a variable voltage to the measuring element during the heating phase.

18. The sensor as in claim 17,
wherein the variable voltage ramps up over time.

* * * * *